(12) United States Patent
Payne

(10) Patent No.: US 8,342,249 B2
(45) Date of Patent: Jan. 1, 2013

(54) OFFSHORE DRILLING SYSTEM

(75) Inventor: Michael L. Payne, Katy, TX (US)

(73) Assignee: BP Corporation North America Inc., Houston, TX (US)

( * ) Notice: Subject to any disclaimer, the term of this patent is extended or adjusted under 35 U.S.C. 154(b) by 175 days.

(21) Appl. No.: 12/840,658

(22) Filed: Jul. 21, 2010

(65) Prior Publication Data

US 2011/0017511 A1    Jan. 27, 2011

Related U.S. Application Data

(60) Provisional application No. 61/228,094, filed on Jul. 23, 2009.

(51) Int. Cl.
*E21B 7/12* (2006.01)
(52) U.S. Cl. ........ 166/358; 166/351; 166/367; 166/368; 175/5
(58) Field of Classification Search .................. 166/358, 166/359, 367, 366, 352, 354; 175/10, 5–8
See application file for complete search history.

(56) References Cited

U.S. PATENT DOCUMENTS

| | | | |
|---|---|---|---|
| 3,603,409 A * | 9/1971 | Watkins | ............................ 175/7 |
| 3,752,326 A | 8/1973 | Levingston | |
| 3,763,809 A | 10/1973 | Pazos | |
| 3,802,209 A | 4/1974 | Weaver | |
| 3,973,635 A | 8/1976 | Gatlin et al. | |
| 4,149,603 A | 4/1979 | Arnold | |
| 4,174,628 A | 11/1979 | van den Bussche et al. | |
| 4,305,468 A | 12/1981 | Goldsmith | |
| 4,435,108 A | 3/1984 | Hampton | |
| 4,602,894 A | 7/1986 | Lorenz et al. | |
| 4,715,761 A | 12/1987 | Berry et al. | |
| 4,813,495 A * | 3/1989 | Leach | ............................... 175/6 |

(Continued)

FOREIGN PATENT DOCUMENTS

GB    2041836 A1    9/1980

(Continued)

OTHER PUBLICATIONS

Hall, J.E., et al., "Use of the Dual-Activity Drillship as a Field Development Tool", 31st Annu. Spe et al. Offshore Technol. Conf. (Houston May 3-Jun. 1999) Proc. V2, pt.2, pp. 13-27, 1999. (OTC-10891 ; 1 ref), publisher name and.

(Continued)

*Primary Examiner* — Matthew Buck
*Assistant Examiner* — Aaron Lembo
(74) *Attorney, Agent, or Firm* — Barbara A. Fisher

(57) ABSTRACT

According to one or more aspects of the invention, a method for drilling an offshore wellbore into a seabed from a platform positioned proximate to the water surface comprises making-up a first tubular string with a first conveyance assembly and running the first tubular string into the wellbore with the first conveyance assembly, wherein the first tubular string enters the wellbore from the water column at an entry position proximate to the seabed; performing a wellbore task with the first tubular string; while the wellbore task is being performed with the first tubular string, making-up a second tubular string in the water column from a second conveyance assembly; withdrawing the first tubular string from the wellbore with the first conveyance assembly once the wellbore task is completed; and running the second tubular string with the second conveyance assembly into the wellbore at the entry point from the water column.

24 Claims, 23 Drawing Sheets

U.S. PATENT DOCUMENTS

| | | | |
|---|---|---|---|
| 4,819,730 A | | 4/1989 | Williford et al. |
| 4,987,956 A | | 1/1991 | Hansen et al. |
| 5,184,686 A | | 2/1993 | Gonzalez |
| 5,195,848 A | | 3/1993 | Huete et al. |
| 5,207,534 A | | 5/1993 | Brasted et al. |
| 5,423,632 A | | 6/1995 | Ekvall et al. |
| 5,458,199 A | * | 10/1995 | Collins et al. ............... 166/313 |
| 5,467,833 A | | 11/1995 | Crain |
| 5,486,070 A | | 1/1996 | Huete |
| 5,647,443 A | | 7/1997 | Broeder |
| 5,865,260 A | * | 2/1999 | Jackson et al. .................. 175/5 |
| 6,056,071 A | | 5/2000 | Scott et al. |
| 6,068,069 A | | 5/2000 | Scott et al. |
| 6,085,851 A | | 7/2000 | Scott et al. |
| 6,142,236 A | | 11/2000 | Brammer et al. |
| 6,216,799 B1 | | 4/2001 | Gonzalez |
| 6,217,258 B1 | | 4/2001 | Yamamoto et al. |
| 6,352,114 B1 | | 3/2002 | Toalson et al. |
| 6,367,554 B1 | | 4/2002 | Theiss |
| 6,394,195 B1 | * | 5/2002 | Schubert et al. ................ 175/69 |
| 6,401,823 B1 | * | 6/2002 | Gonzalez et al. ............. 166/319 |
| 6,443,240 B1 | | 9/2002 | Scott |
| 6,581,698 B1 | | 6/2003 | Dirks |
| 6,601,649 B2 | | 8/2003 | Beato et al. |
| 6,609,573 B1 | | 8/2003 | Day |
| 6,719,059 B2 | | 4/2004 | Dezen et al. |
| 6,745,851 B1 | | 6/2004 | Edvardsen |
| 6,766,860 B2 | | 7/2004 | Archibald et al. |
| 7,431,081 B2 | | 10/2008 | Stave |
| 7,628,224 B2 | * | 12/2009 | D'Souza et al. .................... 175/5 |
| 7,628,225 B2 | * | 12/2009 | Petersson et al. ................. 175/5 |
| 7,677,329 B2 | | 3/2010 | Stave |
| 7,784,546 B2 | | 8/2010 | Patton |
| 7,975,770 B2 | * | 7/2011 | Keener ......................... 166/358 |
| 2003/0066650 A1 | * | 4/2003 | Fontana et al. ............... 166/358 |
| 2004/0140124 A1 | | 7/2004 | Fenton |
| 2007/0089884 A1 | | 4/2007 | Patton |
| 2007/0163782 A1 | | 7/2007 | Keener |
| 2007/0251725 A1 | | 11/2007 | Banks |
| 2008/0000685 A1 | | 1/2008 | Humphreys |
| 2008/0135233 A1 | | 6/2008 | Horton et al. |
| 2008/0190663 A1 | | 8/2008 | Stave |
| 2008/0267716 A1 | | 10/2008 | Souza et al. |
| 2009/0032301 A1 | | 2/2009 | Smith et al. |
| 2009/0114443 A1 | | 5/2009 | Talamo et al. |
| 2009/0220306 A1 | | 9/2009 | Roodenburg et al. |
| 2009/0314495 A1 | | 12/2009 | Schott, III et al. |
| 2010/0098498 A1 | | 4/2010 | Humphreys |

FOREIGN PATENT DOCUMENTS

| | | |
|---|---|---|
| WO | 2008118914 A1 | 10/2008 |
| WO | 2009/018448 A2 | 2/2009 |
| WO | 2009/018448 A3 | 4/2009 |
| WO | 2009/018448 A9 | 9/2009 |

OTHER PUBLICATIONS

PCT International Search Report and PCT Written Opinion of the International Searching Authority issued in related application No. PCT/US2010/042731, mailed Mar. 23, 2011, 10 pages.

Ghiselin D.: "Rigs Drilling on the Double", Petroleum Engineer International, Hart Publications, US, vol. 74, No. 4, Apr. 1, 2001, pp. 71-73, XP001044026, ISSN: 0164-8322, 4 pages.

Stegeman S. et al.: "How the Dual Activity Drillfloor is Expected to Operate", Offshore, Pennwell, Tulsa, OK, US, vol. 59, No. 4, Apr. 1, 1999, XP000831800, ISSN: 0030-0608, 6 pages.

Webb et al.,"Dual Activities Without the Second Derrick—A Success Story", International Association of Drilling Contractors/Society of Petroleum Engineers, IADC/SPE 112869, Mar. 2008, p. 1-24, IADC/Society of Petroleum Engineers Inc., United States.

Keener et al., "Transocean's 5th gen rigs efficient record-setters", Drilling Contractor, May/Jun. 2003, pp. 10-11, vol. 59, No. 3, unknown publisher and place of publication.

D'Souza et al., "A new generation deepwater field development system", Offshore Magazine, Sep. 2002, pp. 50, 52, 128, vol. 62, No. 9, unknown publisher and place of publication.

Nergaard et al., "The Potential of Simultaneous Two-Well Operations from Dual Rig New Generation Drilling Units", Brazil. Petrol. & Gas Inst. Rio Oil & Gas Conf., Oct. 2000, pp. 1-7, IBP 10000, Brazil Petrol. & Gas Institute, Brazil.

Shanks, "Dual activity drilling turns in 20-40% time savings", Drilling Contractor, Sep./Oct. 2001, pp. 26-28, vol. 57, No. 5, unknown publisher and place of publication.

* cited by examiner

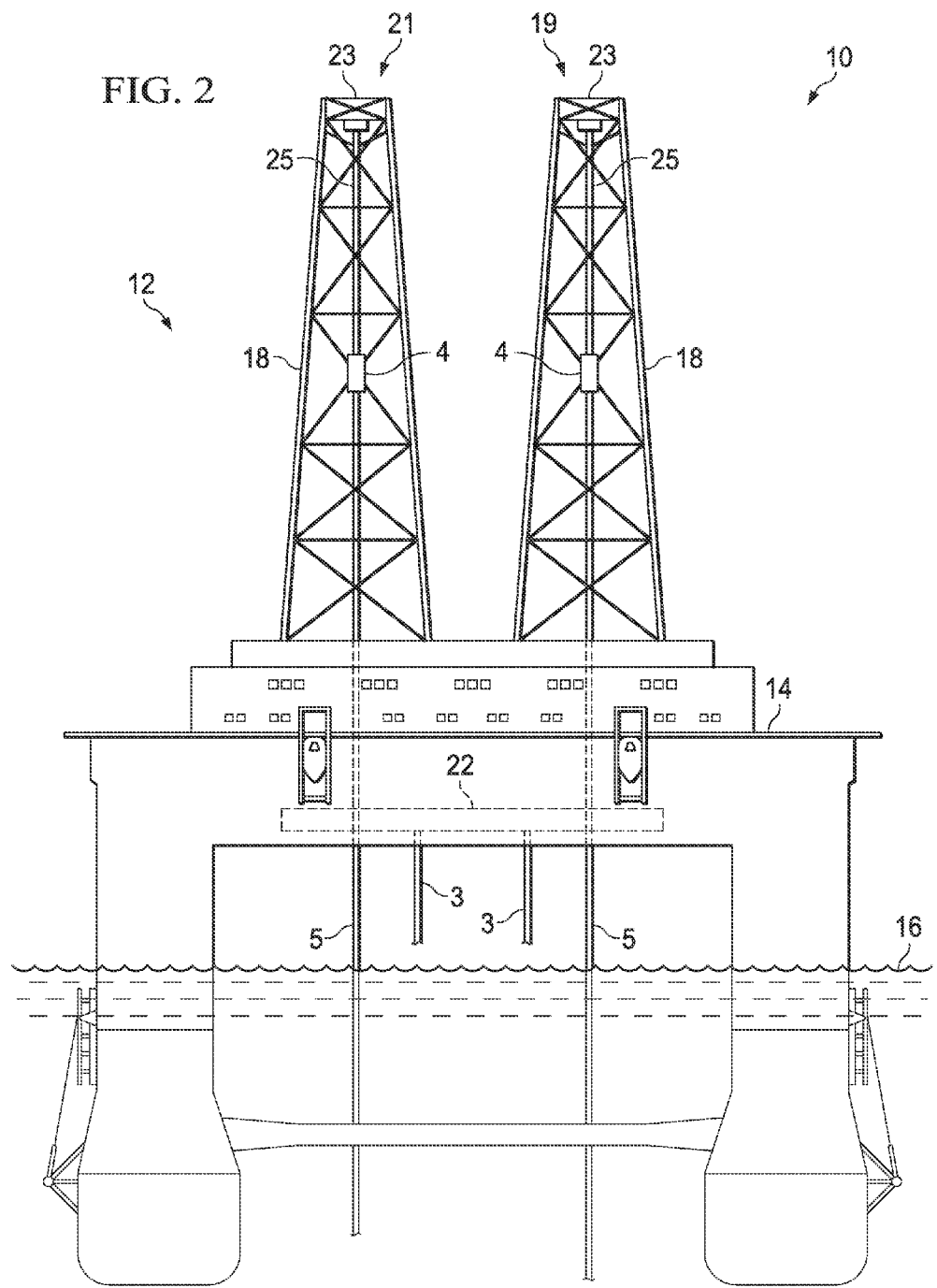

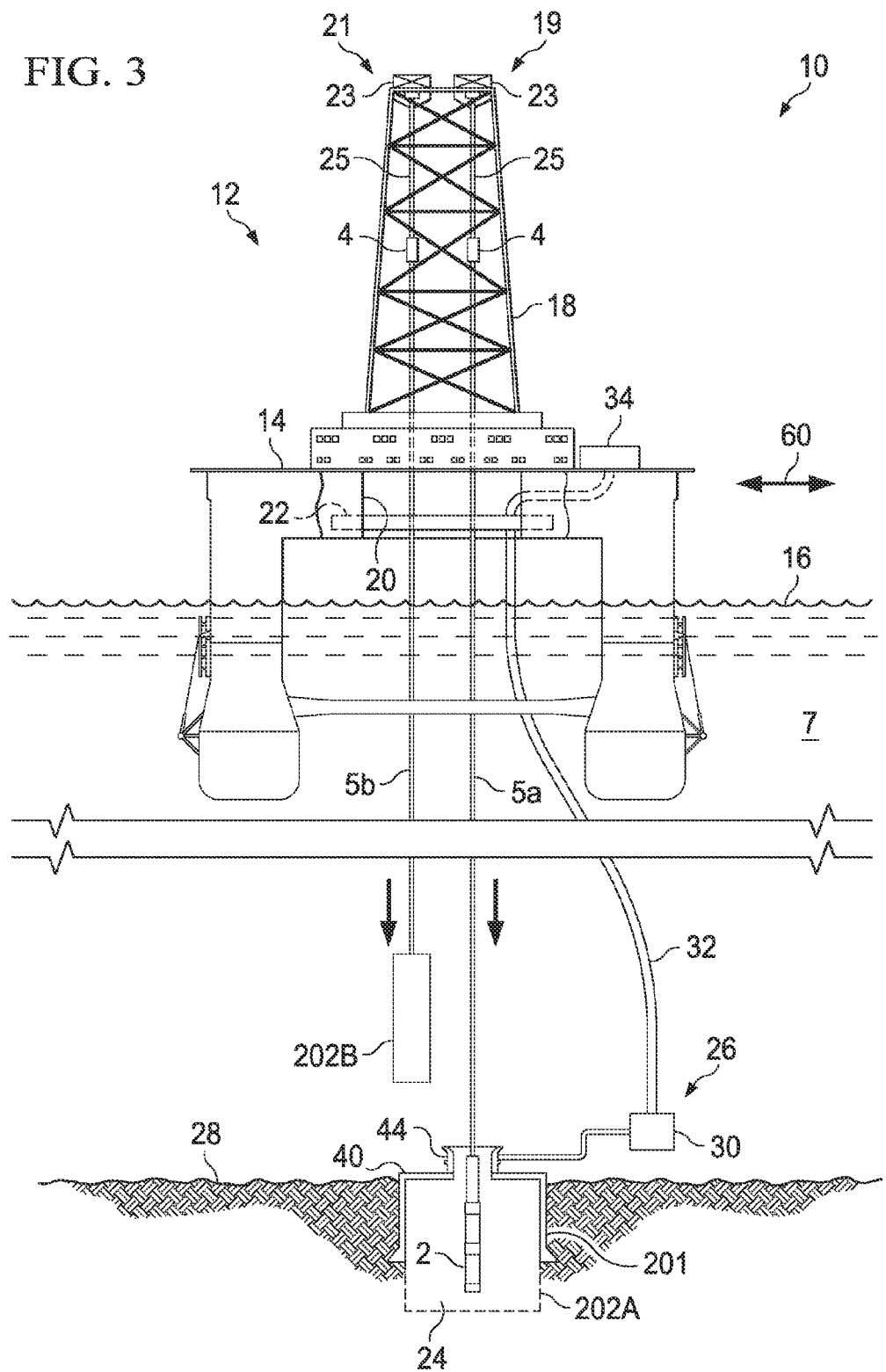

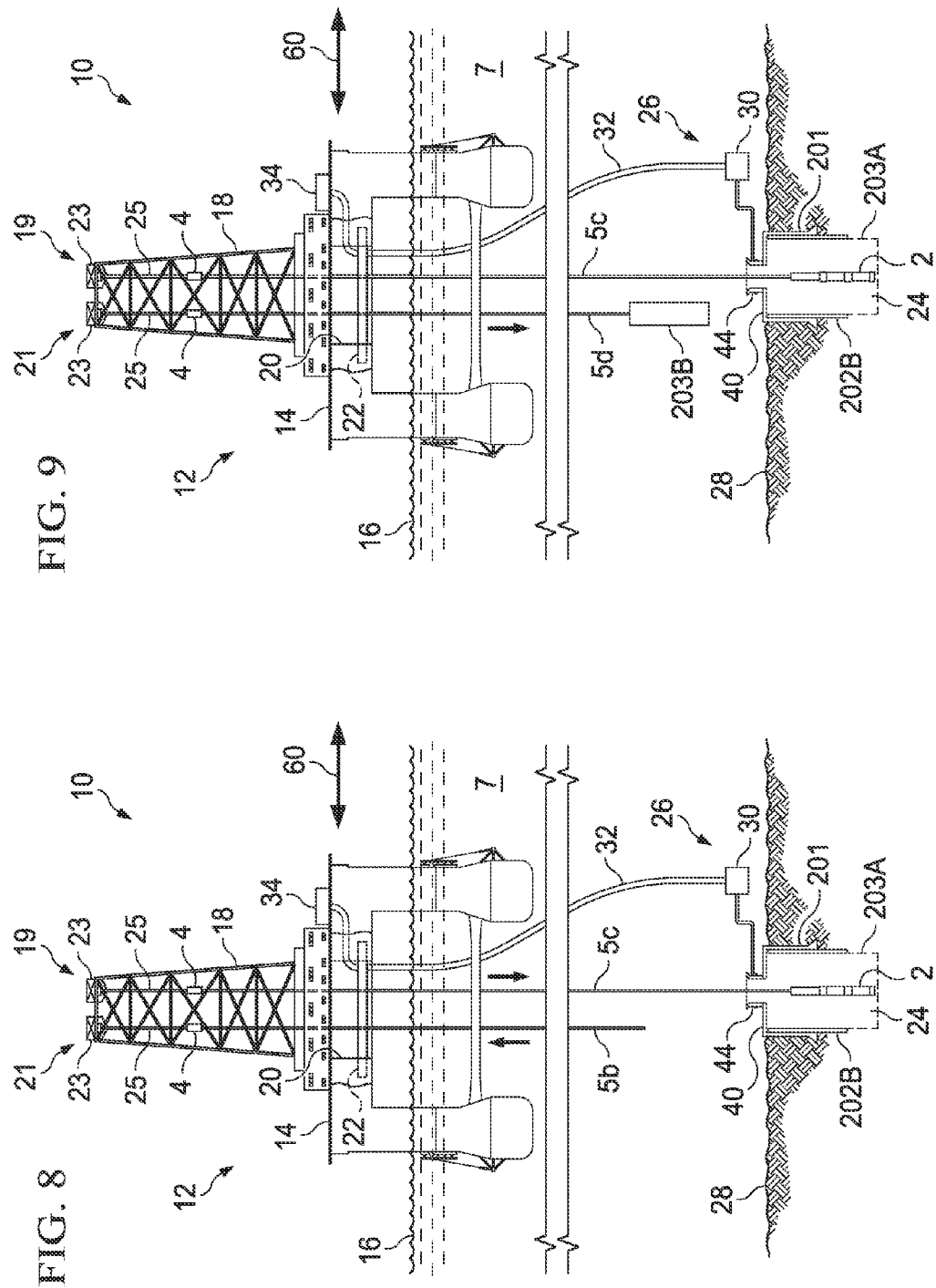

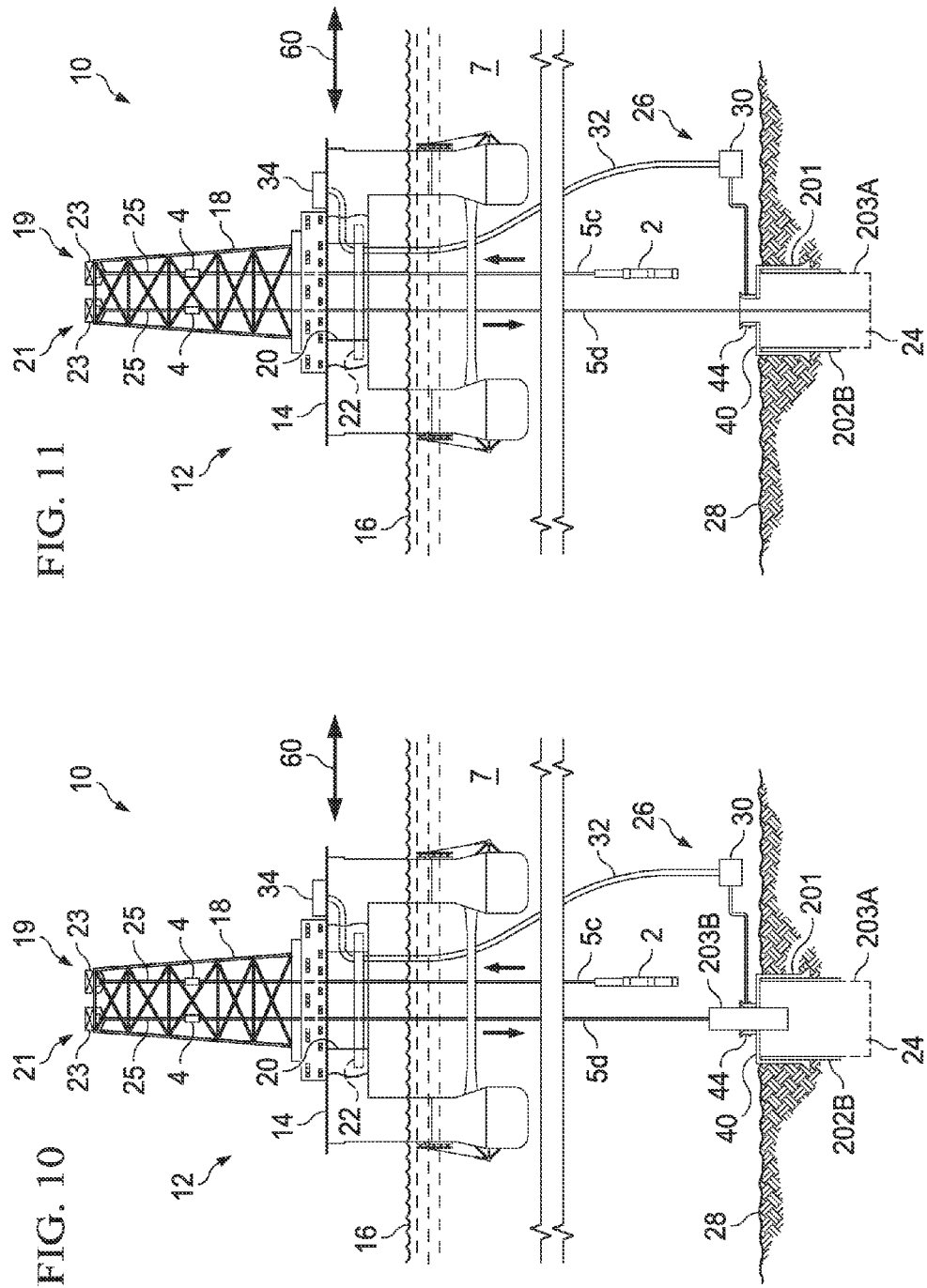

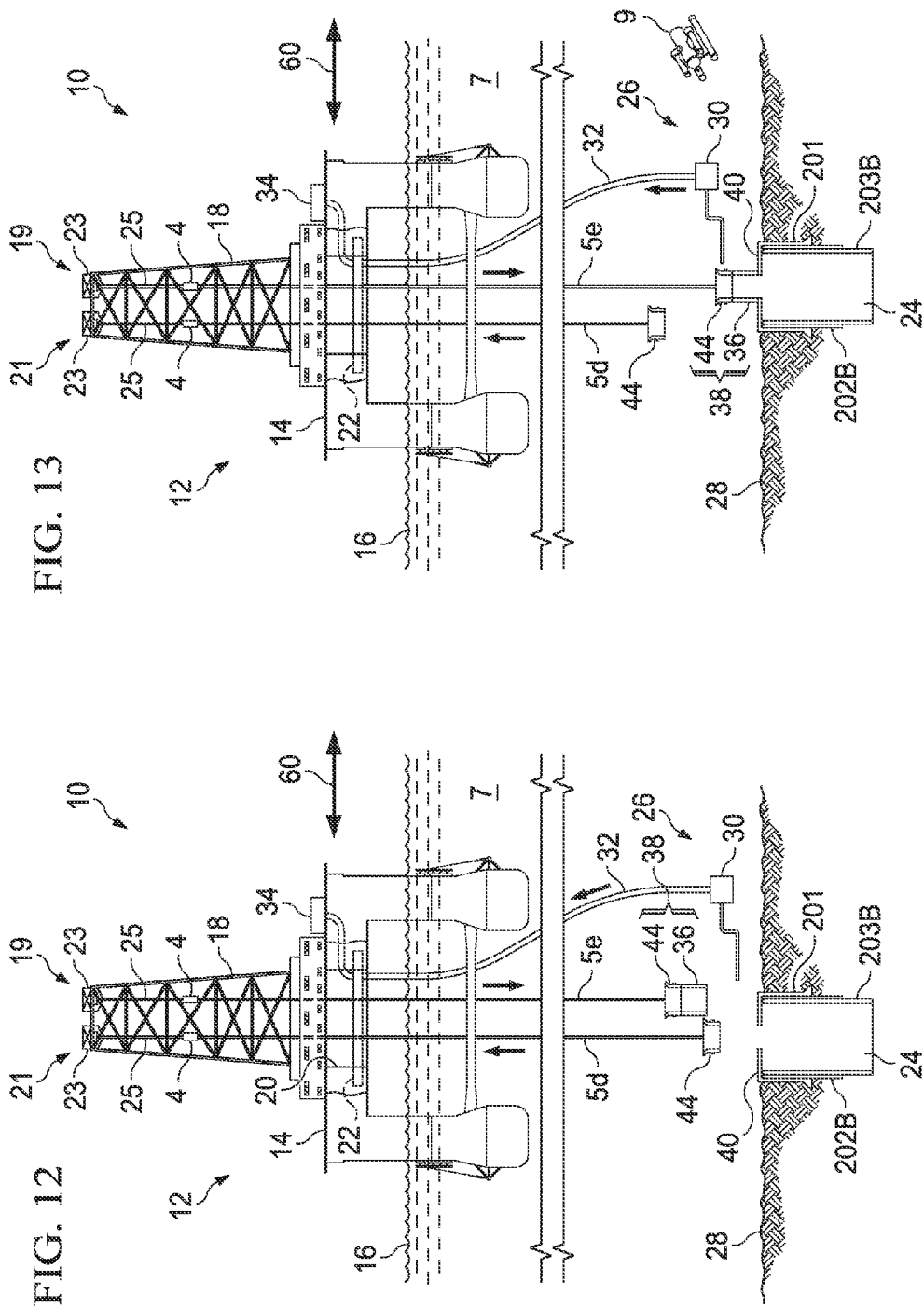

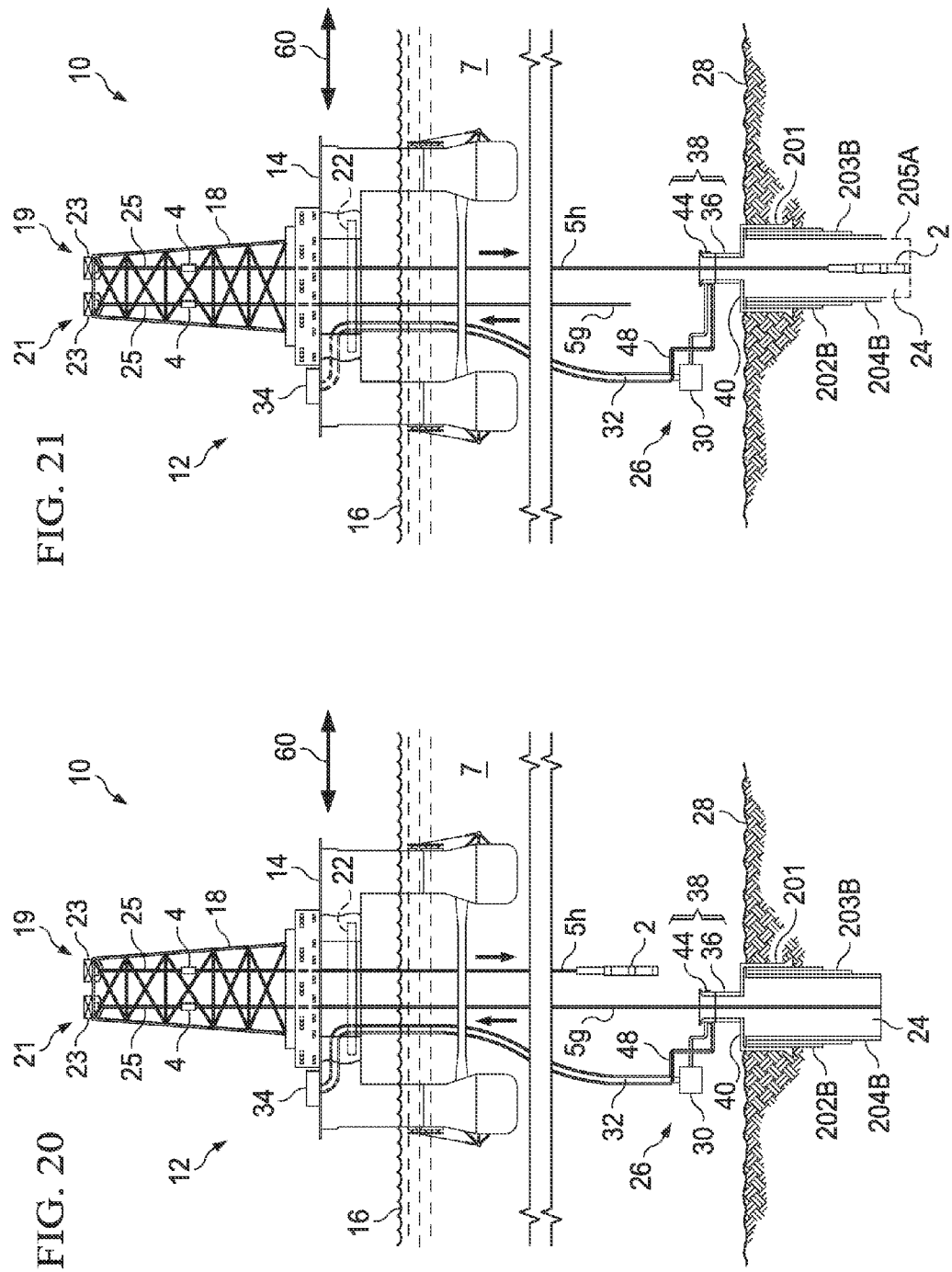

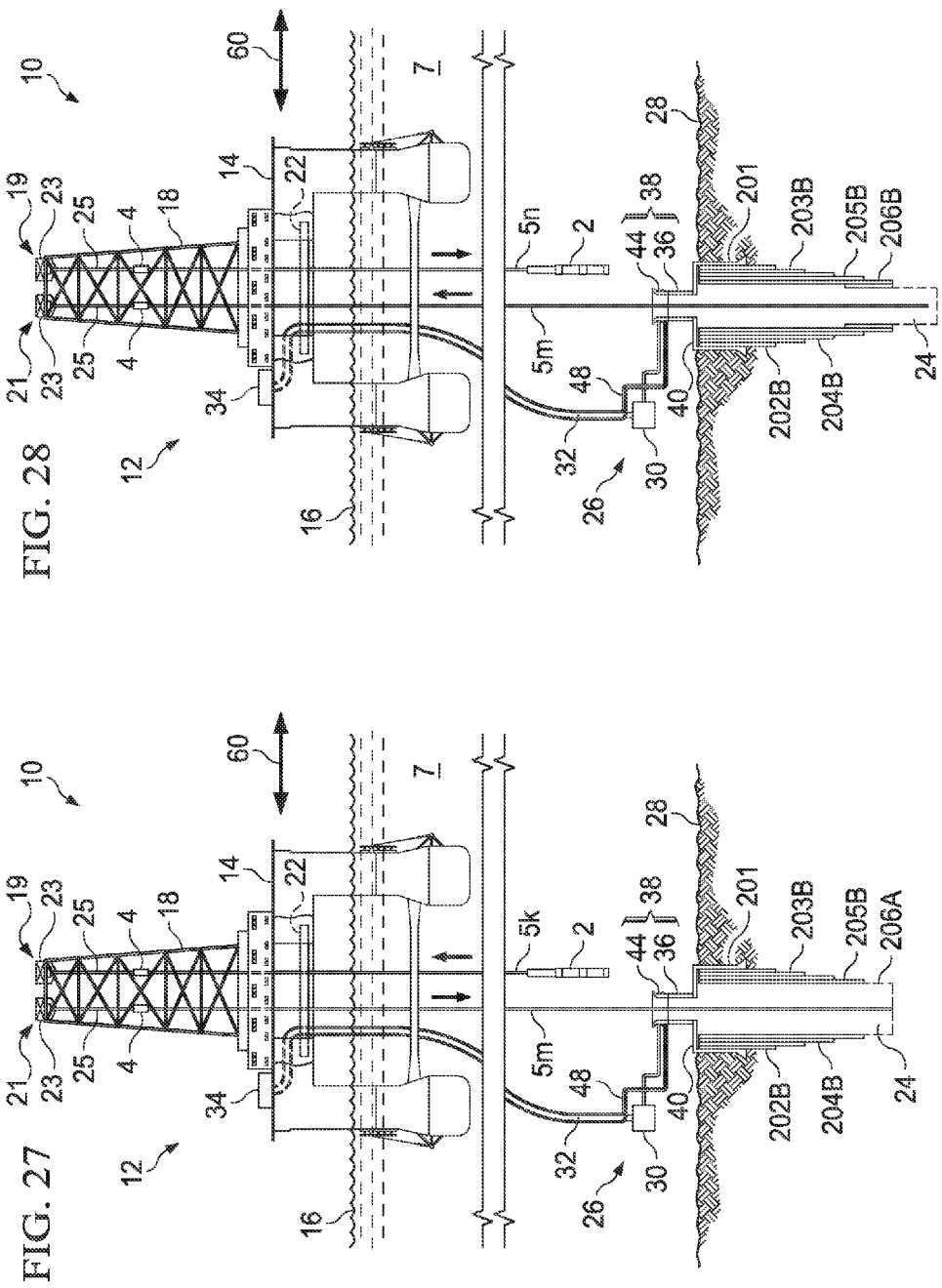

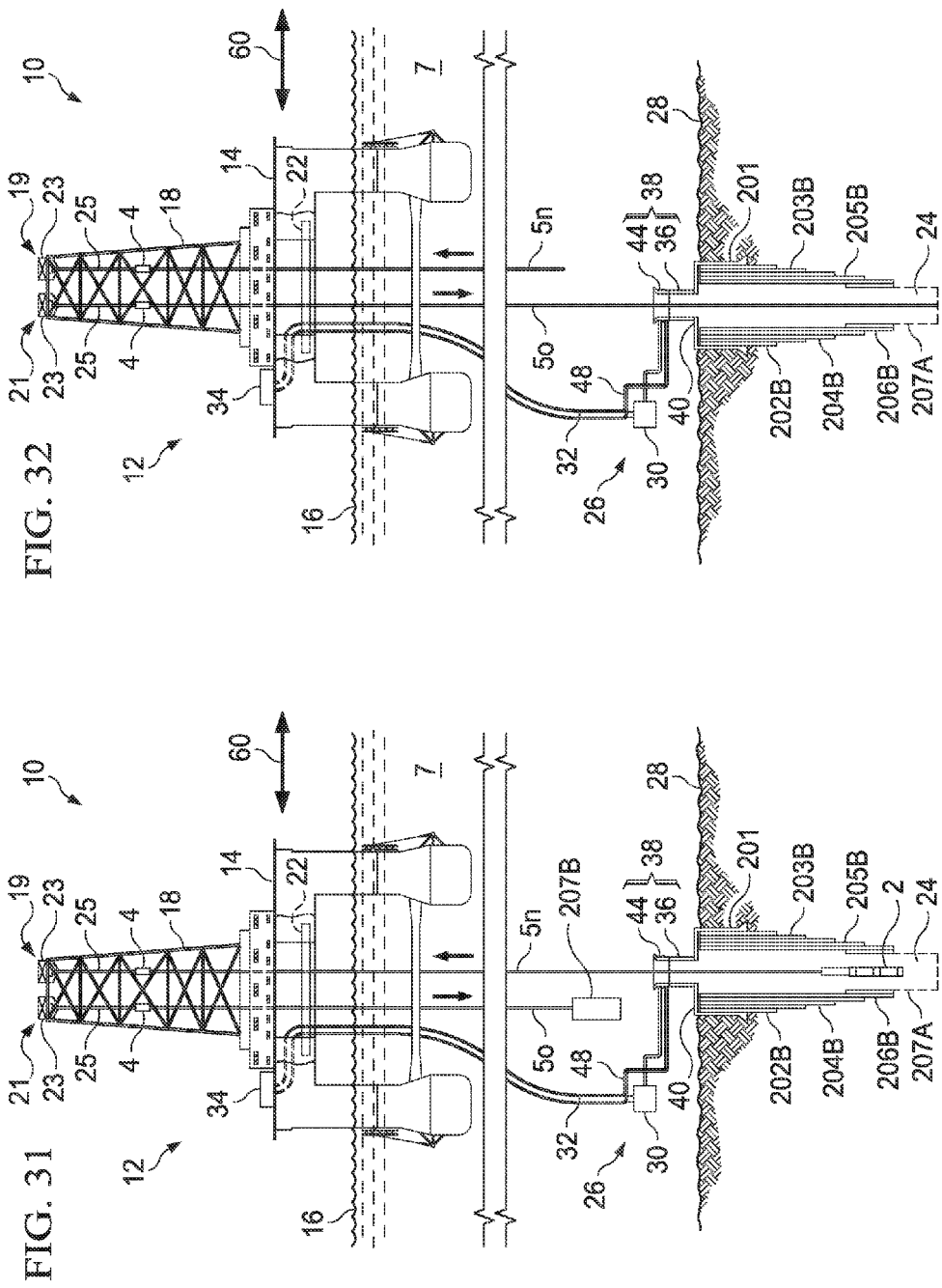

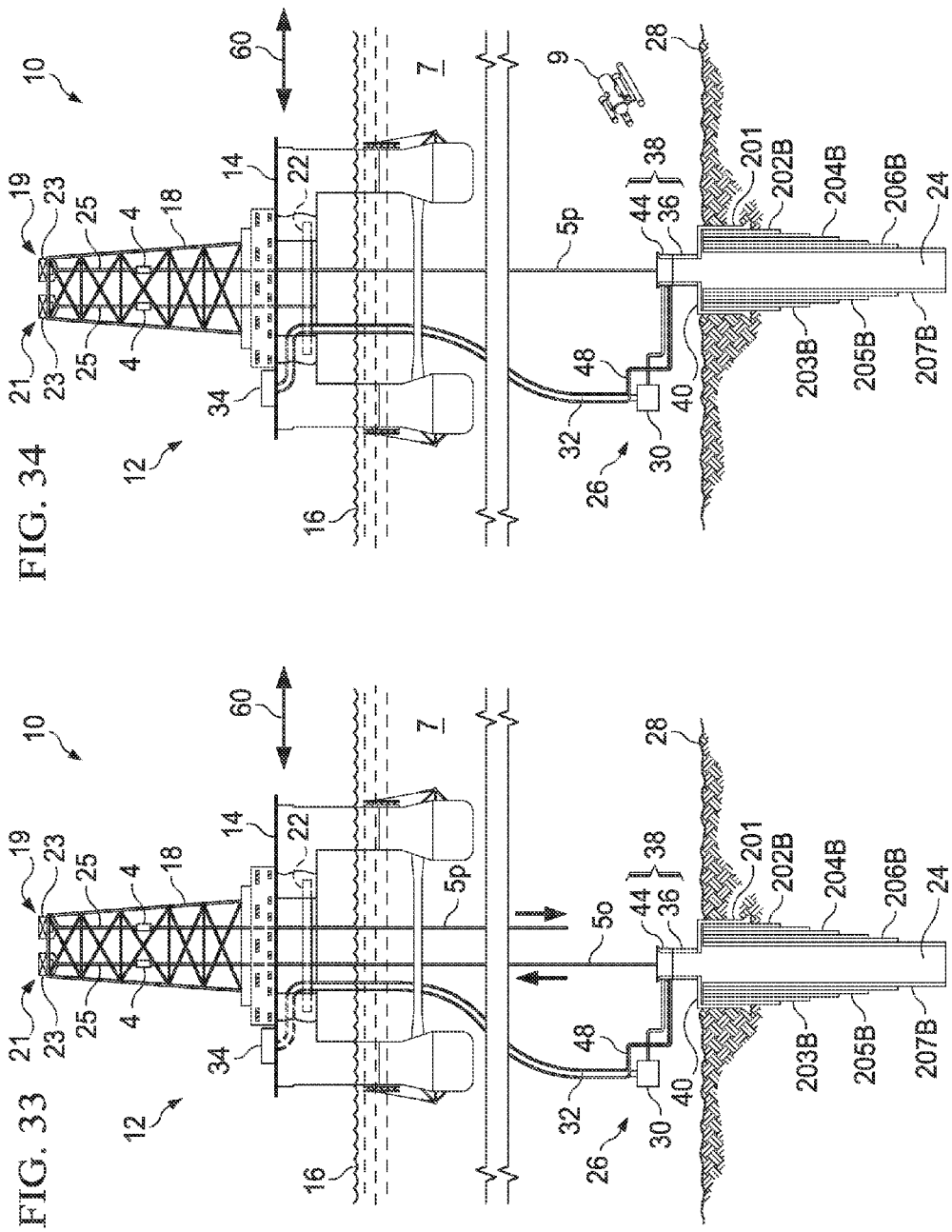

OFFSHORE DRILLING SYSTEM

RELATED APPLICATIONS

This application claims the benefit of U.S. Provisional Patent Application No. 61/228,094 filed on Jul. 23, 2009.

BACKGROUND

This section provides background information to facilitate a better understanding of the various aspects of the present invention. It should be understood that the statements in this section of this document are to be read in this light, and not as admissions of prior art.

Significant oil and gas reserves have been discovered, and continue to be discovered, beneath various bodies of water throughout the world. In the past, technology limited offshore drilling and production to relatively shallow locations in shoreline areas where the depth of the water ranged from a few feet to several hundred feet. Presently the industry has conducted drilling operations in water depths that exceed more than 10,000 feet, and it is anticipated that these operations may continue to move to even deeper waters.

Whenever drilling operations are conducted in deep water, greater costs and logistical challenges are encountered as compared to operations in shallower depths of water. One major cost of drilling and producing a well is simply the cost of leasing the platform and other equipment. Each day of rig time can cost hundreds of thousands of dollars. As such, drilling operations should be planned and designed to run as efficiently as possible. These increased costs are compounded by the additional time needed to deal with the challenges of operating in deep water environments, and the make-up and break-out of tubulars during a conventional drilling operation, for example.

Offshore drilling operations comprise three general phases. The initial phase (e.g., top hole drilling phase) comprises constructing the wellbore in the shallow formations below the seabed prior to installing a blowout preventer ("BOP"). In the top hole drilling phase, an upper portion of the wellbore is formed, for example by jetting and/or drilling a hole, and then a section of casing, referred to generally as a conductor, is positioned and cemented or jetted in the hole. The initial section of the wellbore may comprise one or more sections of casing which typically decrease in diameter (e.g., a tapered string) as the depth increases from the surface of the earthen formations (e.g., the seabed). For example, the top hole section may comprise a first (e.g., top) section having a casing diameter of about 30 inches (66 cm) extending from the seabed to about 300 to 400 feet, and a second section having a casing diameter of about 20 inches (44 cm) extending down from the seabed to about 4,000 feet.

The second phase, referred to herein as the primary drilling phase or the bottomhole drilling phase, is performed after the BOP is installed. Once the top hole section is completed with a conductor and a wellhead, the BOP is conveyed from the drilling platform down through the water column on a riser (e.g., marine riser) and is landed on the wellhead. Risers comprise a large diameter tubular string, for example, having a 21 inch (46.2 cm) outside diameter ("OD"), that provides a conduit from the wellbore, via the BOP, to the surface of the water column located proximate to the drilling platform. Traditionally, the bottomhole drilling phase is performed through the riser. For example, after the BOP is installed, the drillstring is made-up at the drilling platform and run into the wellbore through the riser. Actuation of the drill bit, which is a component of the bottomhole assembly ("BHA"), is conventionally performed through the riser, and the riser is also used to circulate the drilling fluid (e.g., drilling mud). When a section of the wellbore is drilled (or a tool failure occurs), the drilling string is pulled out of the wellbore via the riser to the drilling platform. Additionally, operations including without limitation, drilling, running casing, cementing casing, well testing, well logging, well stimulations, formation fracturing, and the like which are all traditionally performed through the riser.

Once the wellbore is drilled and the downhole portion is completed to the desired depth, post drilling operations can be performed. The BOP is then removed and retrieved to the surface, and for a successful well, a downhole production assembly and a tubing string are installed down hole, and a valve tree (e.g., such as a Christmas tree that is comprised of control valves, gauges, and chokes) is installed at the wellhead.

Traditionally, offshore wellbores are formed (e.g., drilled, completed) using a single load path (e.g., derrick, rig, drilling assembly), thus requiring all wellbore tasks (e.g., drilling, completion, stimulations, workovers, etc.) to be performed from a single assembly. Recently, efforts have been made to decrease the time required to drill wells offshore by performing some tasks simultaneously. For example, U.S. Pat. Nos. 6,085,851 and 6,056,071, each to Scott et al., disclose a multi-activity apparatus and method for conducting drilling operations. In general, Scott et al. disclose a drilling platform having dual drilling assemblies (e.g., separate load paths and/or derricks). In the method disclosed in Scott et al., some activities during the top hole drilling phase and the post drilling phase are performed substantially simultaneously by a main derrick and an auxiliary derrick. However, according to Scott et al., drilling operations are performed from a single load path during the bottomhole drilling phase (i.e., after the BOP has been installed).

A multi-activity drilling facility is also disclosed in U.S. Pat. No. 6,766,860 to Archibald et al. The '860 patent discloses an assembly and method for suspending tubular strings prior to being run into the wellbore (e.g., staging operations) and/or for suspending tubulars that have been removed from the riser and the wellbore. In one example of a post drilling operation, the BOP is removed from the wellbore and moved laterally away from the wellbore and is then suspended from the drilling platform, while the valve tree (e.g., Christmas tree) is run down to the seabed and installed at the wellbore. Consistent with other prior art systems, the wellbore tasks (e.g., drilling, casing, logging, testing, cementing, stimulations, workovers, etc.) are performed from a single load path.

Another solution proposed to improve the efficiency of offshore drilling operations is disclosed in U.S. Pat. No. 6,443,240 to Scott. In the '240 patent, two risers extend from the drilling platform and are both connected to the wellbore though the BOP. Tasks and operations such those associated with drilling and completion, for example, and without limitation to, jetting, driving pipe, drilling with pipe (e.g., drillpipe, casing, liners), cementing, setting casing, hanging liners, gravel packing, logging, fluid sampling, formation testing, measuring with sensors, production and/or injection testing, formation stimulation, and fracturing can be conducted through the first riser, while another drilling operation is staged in the second riser. For example, when the first drilling assembly utilized in the first drilling task is withdrawn from the wellbore into the first riser, the second drilling assembly, staged in the second riser, can be run into the wellbore through the second riser. The proposed improvement in efficiency requires installation and maintenance of two riser assemblies.

There is, therefore, a desire to reduce the time required to drill and complete a wellbore. There is a further desire to provide a deep water drilling method and apparatus that can more fully utilize a platform rig assembly with multi-activity exploration and/or production capabilities, as well as completion, testing, workover, and maintenance capabilities. There is a still further desire to provide an apparatus and method for eliminating the use of some physical equipment traditionally required to conduct offshore drilling operations. And, there is yet a still further desire to provide a drilling system that is more efficient thus decreasing the costs associated with leasing capital drilling equipment.

SUMMARY

A method, according to one or more aspects of the invention, for drilling an offshore wellbore into a seabed from a platform positioned proximate to a water surface and above a water column comprises withdrawing, with a first conveyance assembly, a first tubular string from the wellbore into the water column at a location proximate to the seabed; and running, with a second conveyance assembly, a second tubular string into the water column and then the wellbore at the location proximate to the seabed after withdrawing the first tubular string from the wellbore with the first conveyance assembly, wherein each conveyance assembly has a load path and wherein the load path of the first conveyance assembly is laterally offset from the load path of the second conveyance assembly.

In some embodiments the first conveyance assembly and the second conveyance assembly are disposed in a multi-activity derrick.

In some embodiments the method includes performing a task in the wellbore with the first tubular string disposed in the wellbore, and then making-up at least a portion of the second tubular string in a water column between the water surface and the seabed with the second conveyance assembly, while performing the task in the wellbore with the first tubular string. The task includes one selected from the group of drilling, casing, and cementing for example.

The method can further include establishing a drilling fluid return path from the wellbore, whereby the drilling fluid return path is laterally offset from a load path of the first and the second conveyance assemblies. Establishing the offset drilling fluid return path can comprise establishing fluid connection to the wellbore via a valve. In some embodiments the valve can be a blowout preventer.

In some embodiments the method comprises performing a task in the wellbore with the second tubular string disposed in the wellbore, and after completion of the task, withdrawing with the second conveyance assembly, the second tubular string from the wellbore at a location proximate to the seabed; running, with the first conveyance assembly, a subsequent tubular string into the wellbore at the location proximate to the seabed after the second tubular string is withdrawn from the wellbore; and, continuing to run tubular strings into the wellbore in a substantially alternating sequence with the first conveyance assembly and the second conveyance assembly, until the well is completed.

According to one or more aspects of the present invention, an embodiment of a method for drilling an offshore wellbore into a seabed from a platform positioned proximate to the water surface and above a water column comprises positioning a platform comprising a first conveyance assembly and a second conveyance assembly above a desired location of a wellbore; running a first tubular string from a first conveyance assembly into the water column and to the seabed; forming a first wellbore section utilizing the first conveyance assembly and the first tubular string; making-up a second tubular string with the second conveyance assembly in the water column to a position proximate to the seabed, wherein a portion of making-up the second tubular string is performed while the first conveyance assembly is forming the first wellbore section; withdrawing the first tubular string from the wellbore at a location proximate to the seabed with the first conveyance assembly; and, running the second tubular string into the wellbore into the water column at the location proximate to the seabed with the second conveyance assembly, after the first tubular string is withdrawn from the wellbore with the first conveyance assembly.

The method can further include establishing a drilling fluid return path, whereby the drilling fluid path is laterally offset from a load path of the first and the second conveyance assemblies to the wellbore. In some embodiments establishing the offset drilling fluid return path comprises installing a conduit fluidicly connected to the wellbore and fluidicly connecting the conduit to a pump. The pump is positioned below the water surface in some embodiments.

In some embodiments the first wellbore section is formed prior to installing a valve on the wellbore. In some embodiments, the method comprises forming the first wellbore section after installing the valve on the wellbore. After installing the valve on the wellbore, the method can further comprise withdrawing, with the second conveyance assembly, the second tubular string from the wellbore at a location proximate to the seabed; running, with the first conveyance assembly, a subsequent tubular string into the wellbore at the location proximate to the seabed after the second tubular string has been withdrawn from the wellbore; and, continuing to run tubular strings into the wellbore in a substantially alternating sequence with the first conveyance assembly and the second conveyance assembly until the well is completed.

Another method for drilling an offshore wellbore into a seabed from a platform positioned proximate to the water surface and above a water column according to one or more aspects of the invention, comprises making-up a first tubular string with a first conveyance assembly; running the first tubular string into the water column and then into the wellbore, wherein the first tubular string enters the wellbore from the water column at an entry point proximate to the seabed; performing a wellbore task with the first tubular string; making-up at least a portion of a second tubular string in the water column with a second conveyance assembly, while the task is being performed in the wellbore with the first tubular string; once the wellbore task has been performed with the first tubular string, withdrawing the first tubular string from the wellbore and into the water column with the first conveyance assembly; and, running the second tubular string into the wellbore at the entry point from the water column with the second conveyance assembly. In some embodiments, at least a portion of the making-up of the second tubular string in the water column is performed simultaneously with the performing of the wellbore task with the first tubular string. According to one or more aspects the entry point into the wellbore is a blowout preventer.

According to one or more embodiments the method further includes withdrawing, with the second conveyance assembly, the second tubular string from the wellbore at the entry point proximate to the seabed; running, with the first conveyance assembly, a subsequent tubular string into the wellbore at the location proximate to the seabed after withdrawing the second tubular string from the wellbore; and, continuing to run tubular strings into the wellbore in a substantially alternating sequence with the first conveyance assembly and the second conveyance assembly until the well is completed.

In some embodiments the method includes returning a drilling fluid from the wellbore via a drilling fluid return conduit that is offset from the load path of the first and the second conveyance assemblies and the wellbore.

In some embodiments the method includes fluidicly connecting the fluid return conduit to the wellbore through a pump and the blowout preventer, wherein the pump is disposed proximate to the seabed; and, controlling an inlet pressure of the returning drilling fluid to the pump in response to a wellbore condition. According to one or more aspects, the method further includes adjusting the pump to lower the inlet pressure of the returning drilling fluid in response to losing drilling fluid in the wellbore.

The foregoing has outlined some of the features and technical advantages of the invention in order that the detailed description of the invention that follows may be better understood. Additional features and advantages of the invention will be described hereinafter and form the basis of the claims of the invention.

BRIEF DESCRIPTION OF THE DRAWINGS

The invention may be best understood from the following detailed description along with the accompanying illustrative figures. It is emphasized that various features are not drawn to scale. In fact, the dimensions of various features may be arbitrarily increased or decreased for clarity of discussion.

FIG. 2 is a schematic view of another platform according to one or more aspects of the invention.

FIG. 3 is a schematic view of an initial part of the top hole drilling phase according to one or more aspects of the invention.

FIG. 8 is a schematic view of a subsequent tubular string disposed in the wellbore, wherein a task is being performed with the first tubular string and conveyance assembly while the second tubular string is being retrieved with the second conveyance assembly, according to one or more aspects of the invention.

FIG. 9 is a schematic view of a subsequent tubular string being made-up in the water column with the second conveyance assembly while a wellbore task is being performed in the wellbore with the first conveyance assembly and associated tubular string, according to one or more aspects of the invention.

FIG. 10 is a schematic view of the tubular string associated with the first conveyance assembly being withdrawn from the wellbore at the seabed, with the tubular string associated with the second conveyance assembly positioned to enter the wellbore at the seabed, according to one or more aspects of the invention.

FIG. 11 is a schematic view of the tubular string associated with the first conveyance assembly being retrieved to the surface, while a wellbore task is being performed with the second conveyance assembly and associated tubular string, according to one or more aspects of the invention.

FIG. 12 is a schematic view depicting completion of the top hole drilling phase and a mud return and blowout preventer module for the bottomhole drilling phase being deployed with the first conveyance assembly, according to one or more aspects of the invention.

FIG. 13 is a schematic view of a mud collection system of the top hole drilling phase being retrieved with the second conveyance assembly, while portions of the bottomhole drilling fluid system are being deployed with the first conveyance assembly, according to one or more aspects of the invention.

FIG. 20 is a schematic view of a tubular string being retrieved by the second conveyance assembly and another tubular string being made-up in the water column with the first conveyance assembly, according to one or more aspects of the invention.

FIG. 21 is a schematic view of additional operations being performed substantially simultaneously; while one tubular string is being removed from the wellbore by one conveyance assembly, the other conveyance assembly is running another tubular string into the wellbore in order to perform a wellbore task, according to one or more aspects of the invention.

FIG. 27 is a schematic view of additional operations being performed substantially simultaneously by the conveyance assemblies; while one tubular string is being removed from a wellbore by one conveyance assembly, the other conveyance assembly is running another tubular string into the wellbore, according to one or more aspects of the invention.

FIG. 28 is a schematic view of additional operations being performed substantially simultaneously by the conveyance assemblies; while one conveyance assembly is retrieving a tubular string, the other conveyance assembly is making-up another tubular string, according to one or more aspects of the invention.

FIG. 31 is a schematic view of additional operations being performed substantially simultaneously by the conveyance assemblies; while one tubular string has completed a wellbore task and is being retrieved to the surface by the associated conveyance assembly, another tubular string is being run into the wellbore by the other conveyance assembly, according to one or more aspects of the invention.

FIG. 32 is a schematic view of additional operations being performed substantially simultaneously by the conveyance assemblies; while one conveyance assembly continues to retrieve a tubular string, another tubular string is being run into the wellbore by the other conveyance assembly, according to one or more aspects of the invention.

FIG. 33 is a schematic view of additional operations being performed substantially simultaneously by the conveyance assemblies; while one conveyance assembly is retrieving a tubular string after a wellbore task, the other conveyance assembly is making-up a tubular string, according to one or more aspects of the invention.

FIG. 34 is a schematic view of additional operations being performed substantially simultaneously by the first and the second conveyance assemblies, according to one or more aspects of the invention, whereby tasks are performed in the wellbore by each of the conveyance assemblies in a substantially alternating sequence.

DETAILED DESCRIPTION

Figure 1:
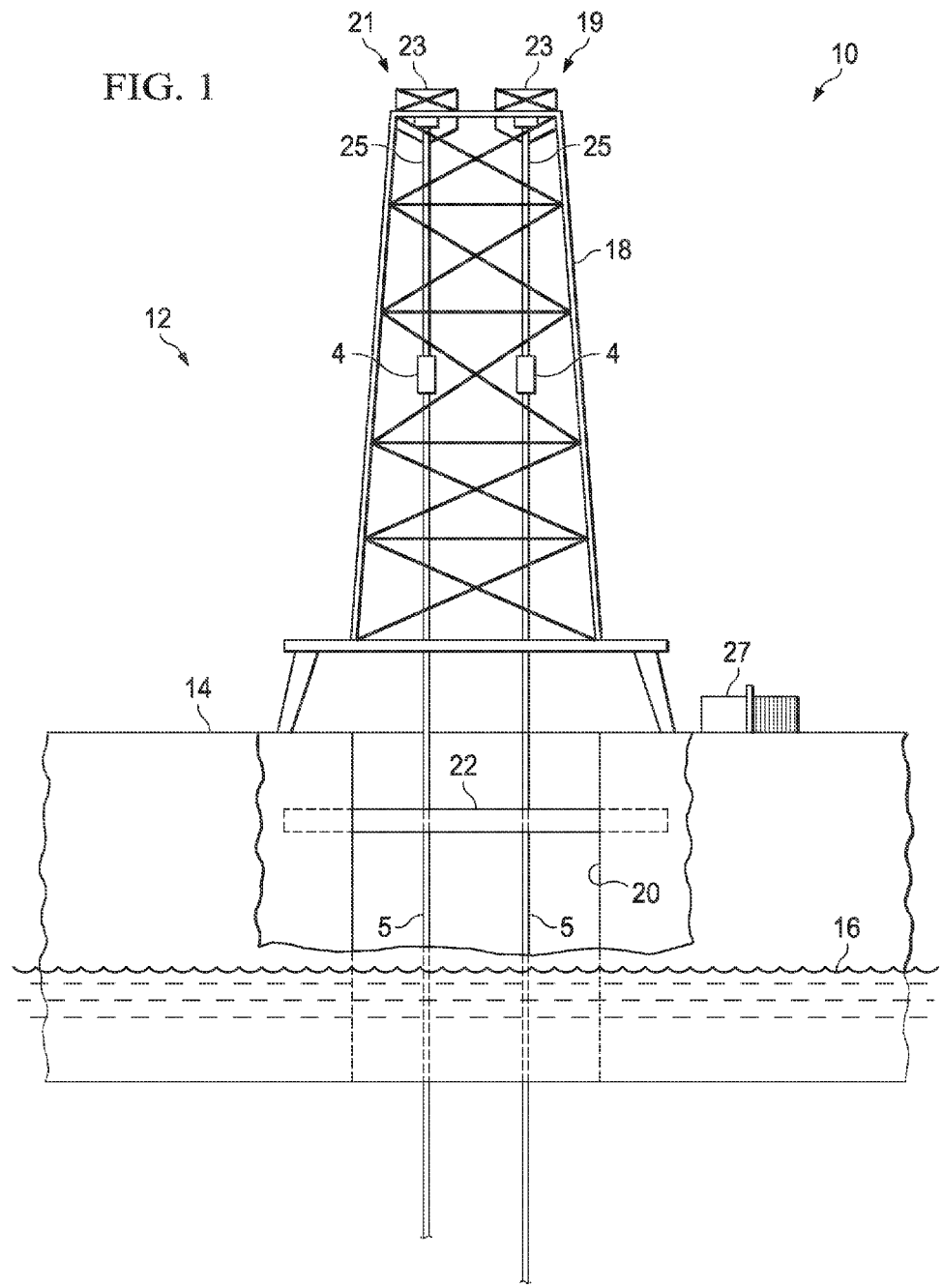
FIG. 1 is a schematic view of a platform according to one or more aspects of the invention.

It is to be understood that the following disclosure provides many different embodiments, or examples, for implementing different features of various embodiments of the invention. Specific examples of components and arrangements are described below to simplify the disclosure. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed.

As used herein, the terms "up" and "down"; "upper" and "lower"; "top" and "bottom"; and other like terms indicating relative positions to a given point or element are utilized in efforts to more clearly describe some elements. The term "tubular" as used herein can mean any type of pipe, unless specifically stated otherwise. The terms may be used in combination with "joint" to mean a single unitary length, or a "string" meaning two or more interconnected joints.

In this disclosure, "fluidicly coupled" or "fluidicly connected" and similar terms, may be used to describe items such as parts, equipment, components, or bodies that are connected in such a way that fluid pressure may be transmitted between and among the connected items. The term "in fluid communication" is used to describe bodies that are connected in such a way that fluid can flow between and among the connected items.

FIG. 1 is a schematic diagram of an offshore wellbore forming system 10 (e.g., drilling system), according to one or more aspects of the disclosure. System 10 comprises a platform, generally denoted by the numeral 12, from which wellbore tasks (e.g., operations) are performed. For example, platform 12 may include, without limitation, drillships, barges, fixed or unfixed platforms, submersible platforms, semi-submersible platforms, tension-leg platforms, and spars. In FIG. 1, platform 12 is depicted as a drillship. Examples of the systems and methods of the invention are described herein for the purposes of clarity and brevity in terms of forming a wellbore (e.g., drilling driving, jetting). As is known in the art, forming the wellbore may comprise many operations such as, and without limitation to, drilling with pipe (e.g., drillpipe, casing, liners), driving pipe, setting and hanging casing (e.g., liners), cementing, gravel packing, logging, measuring with sensors, production testing, injection testing, formation testing, formation stimulation, workover tasks, and other operations associated with the foregoing tasks.

The platform of the depicted drillship 12 comprises a main deck 14 located above the water surface 16, and a derrick 18 positioned over a moon pool 20 which extends through the hull and provides access to the water below, enabling the conveyance assemblies on the platform to raise or lower strings into the water column and conduct operations with the strings. Platform 12 may be referred to as a multi-activity platform which includes more than one conveyance assembly (e.g., hoisting system, load path). Conveyance assembly, or tubular conveyance assembly, is utilized herein to mean an assembly which is suitable to convey strings and equipment to and from the wellbore and to perform wellbore operations. For example, with reference to FIG. 1, platform 12 comprises a single derrick 18 which comprises a first conveyance assembly 19 and a second conveyance assembly 21, which may also be referred to as sub-derricks or mini-derricks, each of which is suitable to make-up and break-out tubular strings 5, as well as perform wellbore operations. For example, each conveyance assembly 19, 21 can include a crown block 23 around which separate cables 25 are run for each conveyance assembly. Cables 25 are maneuvered via drawworks 27. Rotation and/or torque may be transmitted to tubular joints and/or tubular strings via a top drive 4 and/or rotary tables to make-up and break-out tubular connections and to rotate and torque the string of tubulars. Alternatively and in addition, this invention can be carried out using derricks that are housed and operated from different platforms and/or vessels, with each derrick having at least one conveyance assembly.

FIG. 2 is a schematic diagram of another type of platform 12, according to one or more aspects of the present disclosure. Platform 12 depicted in FIG. 2 is a multi-activity platform comprising at least two conveyance assemblies 19, 21 configured as individual derricks 18. Depicted platform 12 is semi-submersible and includes a structure 22 (e.g., rack) from which devices, denoted generally by the numeral 3, may be suspended or hung-off. Devices 3 comprise, without limitation, tubular strings, operational assemblies (e.g., drilling assemblies, bottomhole assemblies, valve assemblies), and drilling fluid return conduits.

Figure 2A:
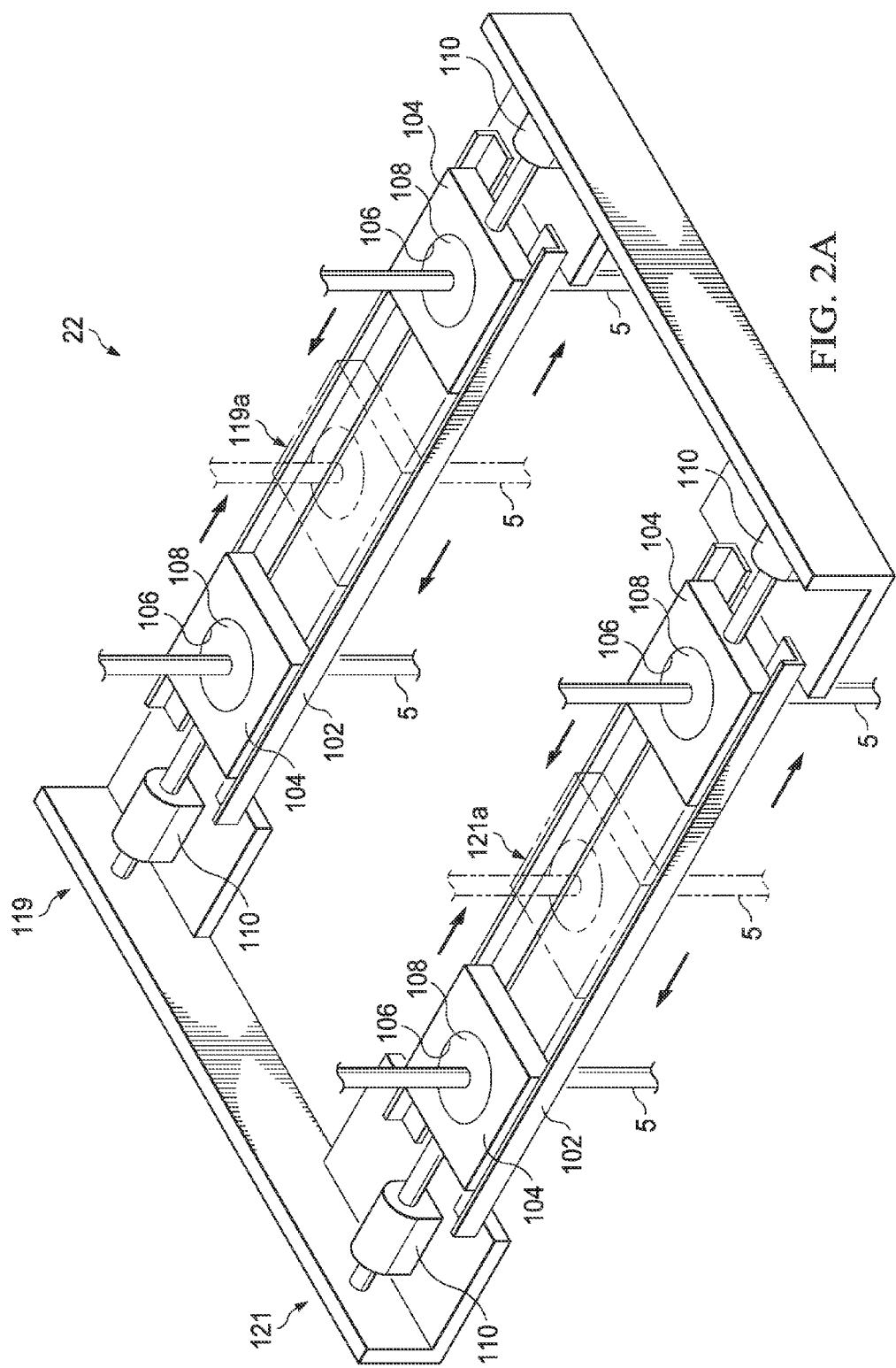
FIG. 2A is a schematic view of a structure, according to one or more aspects of the invention, which can be located below one or more of the conveyance assemblies for hanging off tubular strings and operational devices from the platform; the structure and any stored strings or devices are offset from the load path of the conveyance assemblies.

FIG. 2A is a schematic view of a structure 22, according to one or more aspects of the invention, which can be located below one or more of the platforms or conveyance assemblies. Depicted structure 22 provides two operational paths, each associated with a conveyance assembly. In the depicted embodiment, structure 22 comprises a first track 119 and a second track 121. First track 119 comprises a pair of spaced apart rails 102, which are parallel to one another in the illustrated embodiment and are located below the first conveyance assembly 19 of FIG. 2. Second track 121 similarly comprises a pair of spaced apart rails 102 which are parallel to one another in the illustrated embodiment, and are located below the second conveyance assembly 21 of FIG. 2. Rails 102 may also be oriented in different configurations, such as and without limitation to a V-shape, C-shape, an arc, or triangle. One or more tables 104 are moveably disposed on each track 119, 121. Tables 104 comprise a passage 106 through which a tubular 5 can be disposed. A gripping device 108 (e.g., slips, a spider) is disposed with tables 104 and passages 106 to engage and suspend tubular 5. A driving mechanism 110 is connected with or associated with the tables 104 to move the tables along the respective track 119, 121. Although not illustrated, tables 104 may comprise operational devices to rotate the suspended tubular 5. Driving mechanisms 110 are illustrated as fluidic (e.g., hydraulic) cylinders in the depicted embodiment. However, other driving mechanisms including without limitation motors, winches, and the like may be utilized.

In FIG. 2A, tables 104 are illustrated by hidden lines in a base position (e.g., 119a, 121a). The base position is located below and within the load path of the respective conveyance assembly 19 or 21, illustrated, for example, in FIG. 2. In an embodiment, base station 119a is located below and in the load path of the conveyance assembly 19 of FIG. 2. When desired, a string 5 carried by conveyance assembly 19 can be suspended from the table that is positioned at base station 119a. The suspended string 5 can then be disconnected from conveyance assembly 19 and moved laterally along track 119 to a position (e.g., left or right) offset from the load path (e.g., center/base station) of conveyance assembly 19 in this embodiment. In some embodiments, for example as depicted in FIG. 2A, a second table (or more tables) may be disposed on track 119. Track 121 is similarly configured in this embodiment. Base station 121a is located in the load path of the conveyance assembly 21 of FIG. 2, for example. A tubular string 5 can be suspended from a table 104 and moved laterally away from the load path of the conveyance assembly and then hung-off of structure 22 and platform 12 (FIG. 2), while other tasks can be performed with conveyance assembly 21.

Figure 16:
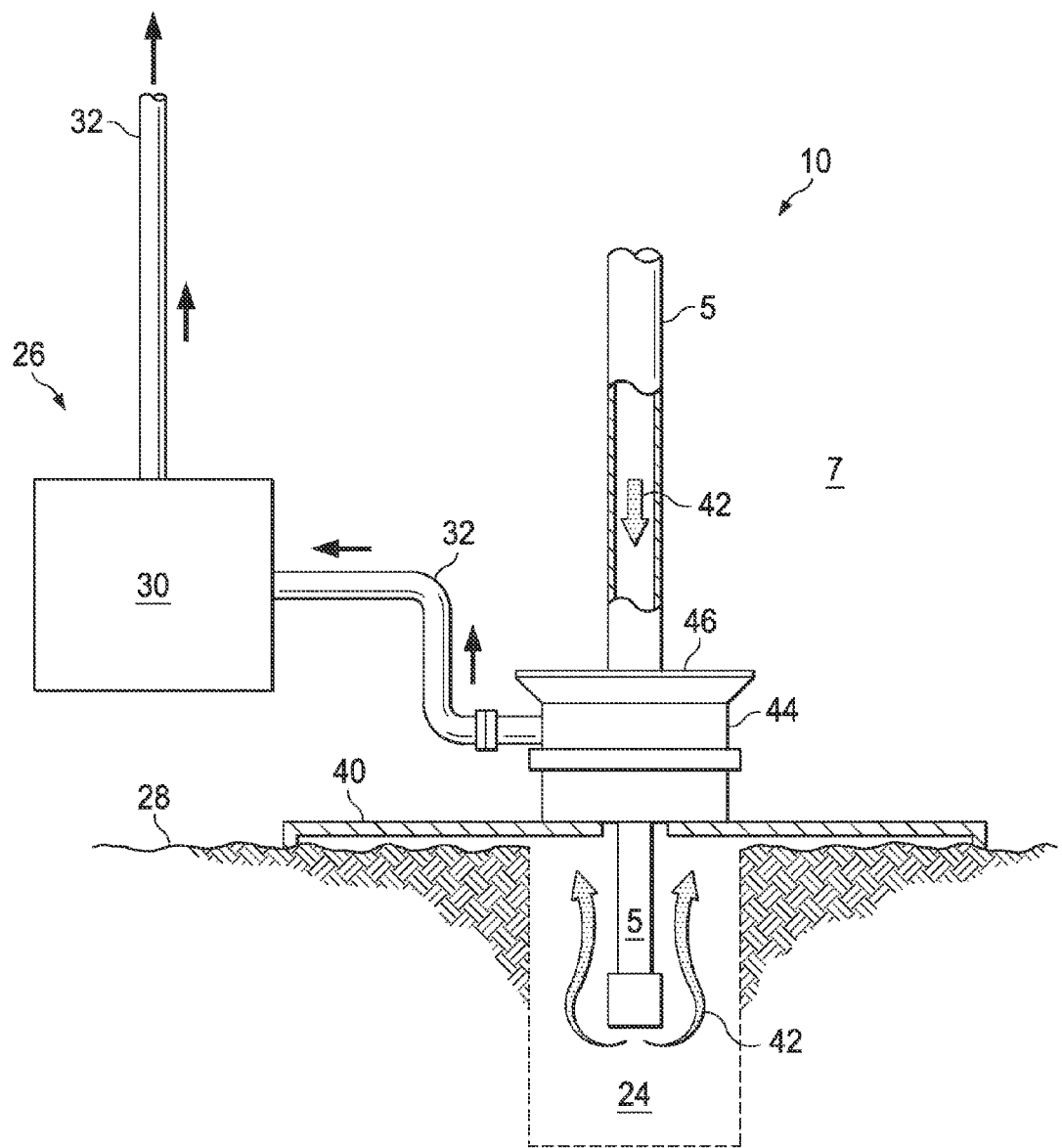
FIG. 16 is a schematic view of a drilling fluid return system utilized for the top hole drilling phase, according to one or more aspects of the invention.
Figure 17:
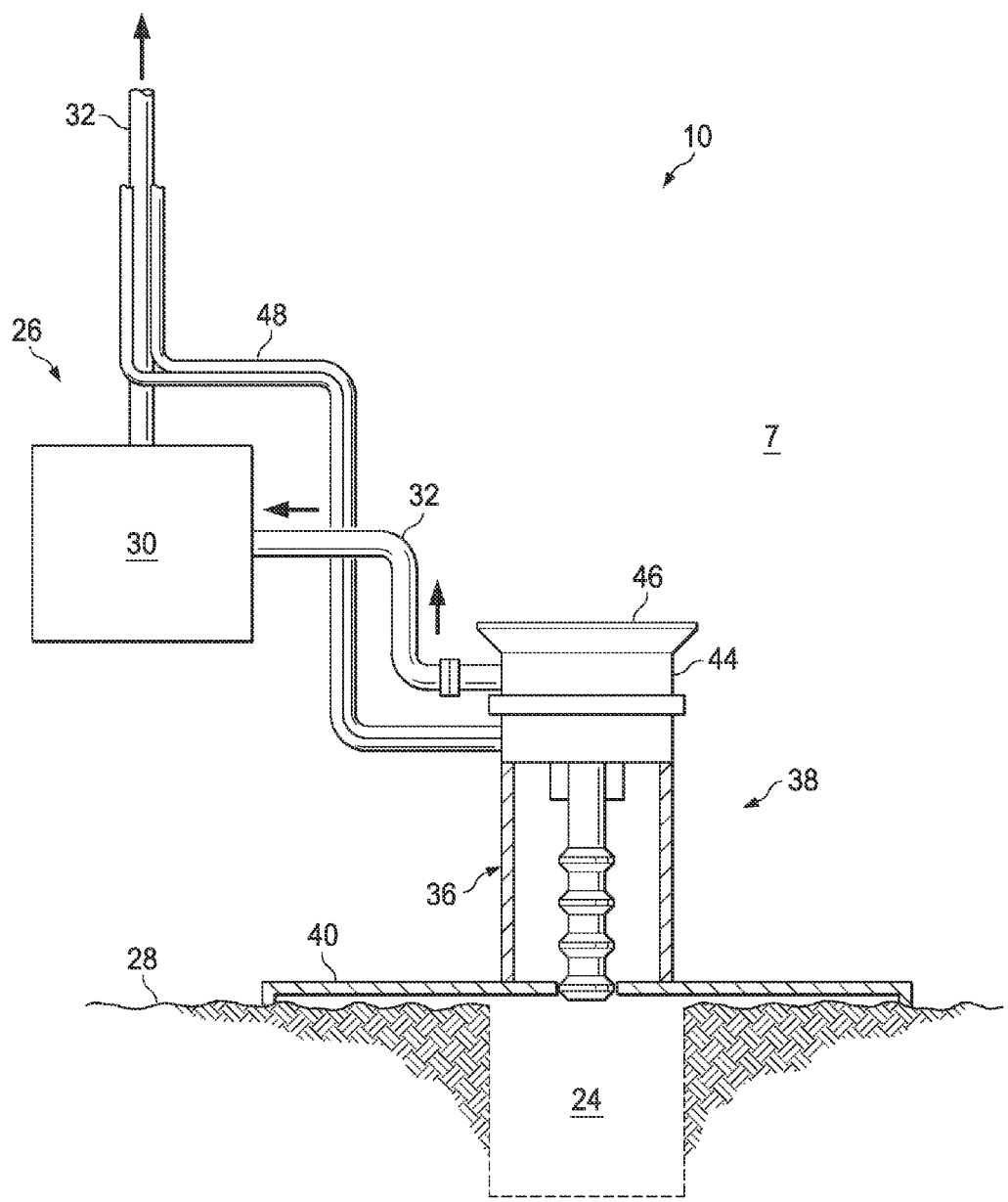
FIG. 17 is a schematic view of a drilling fluid return system utilized for the bottomhole drilling phase, according to one or more aspects of the invention.

Referring now to FIGS. 3-12, a method for forming (e.g., driving, jetting, drilling) a top hole section of a wellbore 24, according to one or more aspects of the invention is described. Platform 12 is positioned at water surface 16 above the desired location for wellbore 24; the platform is equipped with a moon pool 20, which is an opening in the floor or base of the platform that gives access to the water below. A mud return system (e.g., suction and collection system), generally denoted by the numeral 26, is positioned proximate to seabed 28, to facilitate collection of cuttings and/or used drilling fluid resulting from forming wellbore 24, and to transport the cuttings and/or drilling fluid away from the wellbore. In this example, system 26 is provided for utilization while forming the top hole section of the wellbore. For purposes of clarity, the term top hole section, as it is utilized herein, refers to the section of the wellbore that is formed prior to installing a blowout preventer ("BOP"). Mud return system 26 comprises a pump 30, and a mud return conduit 32 in fluid connection with the wellbore 24 and a surface mud collection device 34. Mud return conduit 32 is fluidically connected to wellbore 24 via a subsea mud collection device 44. Non-limiting examples of mud return system 26 are illustrated in FIGS. 16 and 17 below. Surface mud collection device 34 is depicted disposed at platform 12 in the illustrated embodiment, and mud return conduit 32 is hung-off (e.g., connected, suspended) from platform 12, for example, at structure 22 or hung from a crane. In some embodiments, surface mud collection device 34 may be located on a different platform (e.g., ship, barge, etc.) than platform 12. In some embodiments, surface mud collection device 34 may be located on an external buoy from platform 12 utilizing, for example, self buoyant risers and submerged buoyant platforms. Non-limiting examples of self-buoyant risers are disclosed in U.S. Pat. Nos. 3,999,617 and 4,436,451, for example.

Referring now to FIG. 3, a first conductor 201 is driven into seabed 28 initiating wellbore 24, and mud return system 26 is in place. First conveyance assembly 19 is being utilized to make-up a first tubular string 5a comprising a device generally denoted by the numeral 2, in the water column. Simultaneously, utilizing second conveyance assembly 21, a second tubular string 5b comprising a second conductor 202B is made-up in the water column and run toward seabed 28 and wellbore 24 to be set in the wellbore section that will be formed by device 2 of tubular string 5a. Device 2 is schematically depicted as a lower portion of the tubular string for purposes of representing various mechanical, electrical, and/or fluidic devices that may be incorporated within the operational assemblies referred to generally herein as tubular strings. For example, and without limitation, device 2 may comprise one or more of a different diameter or type of tubulars (e.g., casing, liners, etc.), cutters (e.g., drillbit), mud motors, valves, bottomhole assemblies, drill collars, logging instruments, sensors, cementing shoes, and other wellbore related tools and devices. Here, for example, device 2 of tubular string 5a comprises a drilling device (e.g., shoe, jetting assembly, cutter).

Figure 4:
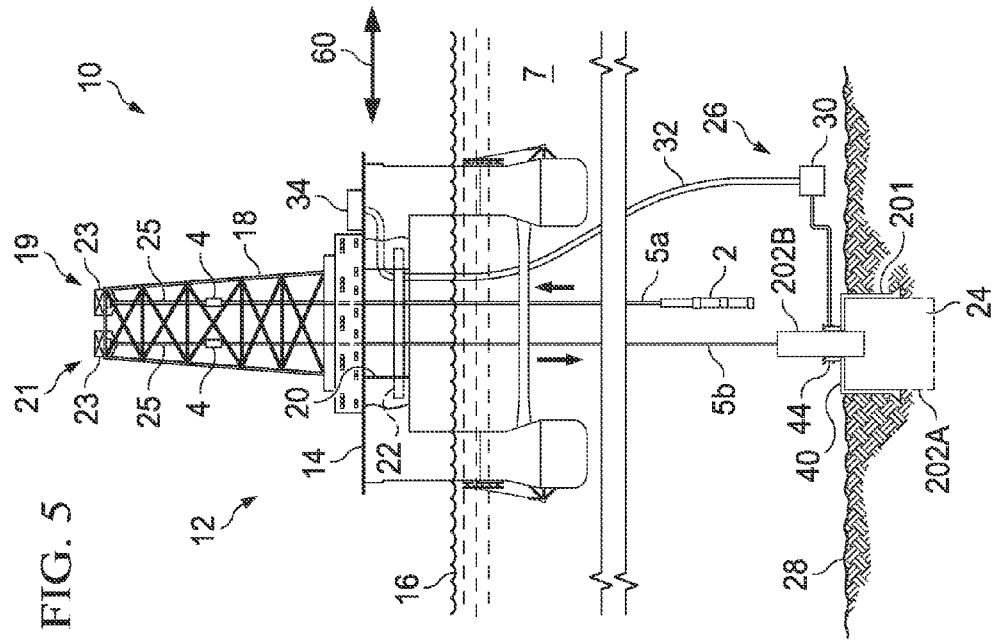
FIG. 4 is a schematic view of a tubular string and first conveyance assembly forming a portion of a wellbore, and a second conveyance assembly making-up a different tubular string, according to one or more aspects of the invention.

In FIG. 4, tubular string 5a and the drilling device of device 2 are being utilized to form (e.g., jet) section 202A of wellbore 24 below first conductor 201. Conveyance assembly 21 continues to make-up tubular string 5b and to run second conductor 202B toward wellbore 24.

Figure 5:
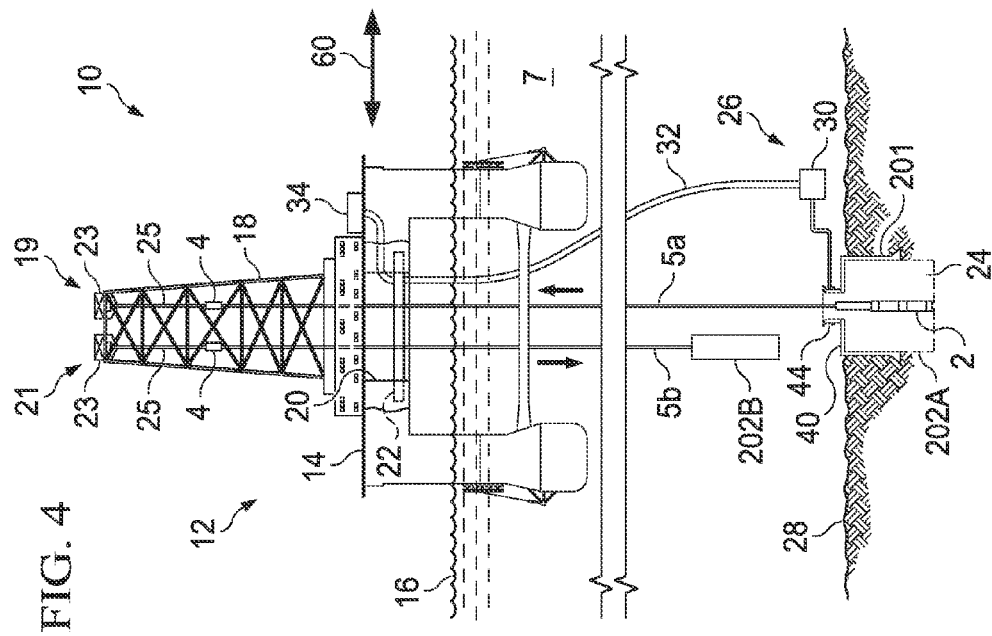
FIG. 5 is a schematic view depicting the first tubular string being pulled out of the wellbore proximate to the seabed, and a second tubular string positioned to enter the wellhead and then be run into the seabed and the wellbore with the second conveyance assembly, according to one or more aspects of the invention.

In FIG. 5, wellbore section 202A has been formed by tubular string 5a, and tubular 5a is depicted being pulled out of the hole or wellbore at wellhead 40 (e.g., proximate to seabed 28) by conveyance assembly 19. Once tubular string 5a has been removed from the wellbore proximate to seabed 28 (e.g., at wellbore 24) and into water column 7, tubular string 5b can be lowered into wellbore 24 from the water column via conveyance assembly 21. In some embodiments it may be necessary to position (e.g., reposition) platform 12, utilizing for example dynamic positioning thrusters, to align a tubular string and the load path of conveyance assembly 19 or 21 that will convey the tubular string with wellbore 24, prior to running the tubular string into the wellbore. For example, with reference to FIG. 5, platform 12 can be repositioned to align tubular string 5b and the load path of conveyance assembly 21 with the wellbore prior to running tubular string 5a into wellbore 24. Movement of platform 12 for purposes of aligning the load paths of conveyance assemblies 19, 21 with wellbore 24 is indicated generally by the arrow 60. The load paths of each conveyance assembly are different.

Figure 6:
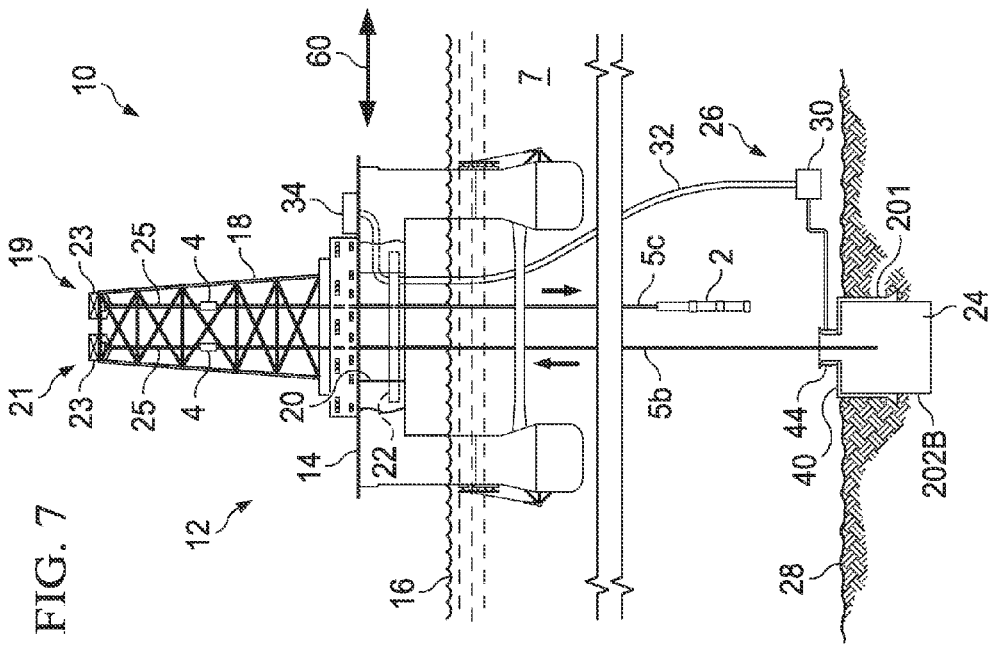
FIG. 6 is a schematic view of the first tubular string being retrieved to the surface with the first conveyance assembly, and simultaneously a wellbore task being performed with the second tubular string and the second conveyance assembly, according to one or more aspects of the invention.

In FIG. 6, tubular string 5a is depicted as being hoisted to platform 12 and then will be disassembled via first conveyance assembly 19. It should also be noted that the tubular string may be disassembled and stored on platform 12, a supply vessel, and/or suspended from structure 22. Simultaneously, utilizing second conveyance assembly 21, tubular string 5b is run into wellbore 24 to level 202A, landing the second conductor. Once the task from each perspective conveyance assembly has been completed, the tubular string associated therewith can be withdrawn and either disassembled and stored or stored as a tubular string (e.g., hung-off of structure 22) so that the next string can be assembled, run into the wellbore, and operated to perform its task. The alternating of operations conducted in the wellbore from the first conveyance assembly and the second conveyance assembly can continue through the top hole drilling phase and the bottomhole drilling phase until the well is completed.

Figure 7:
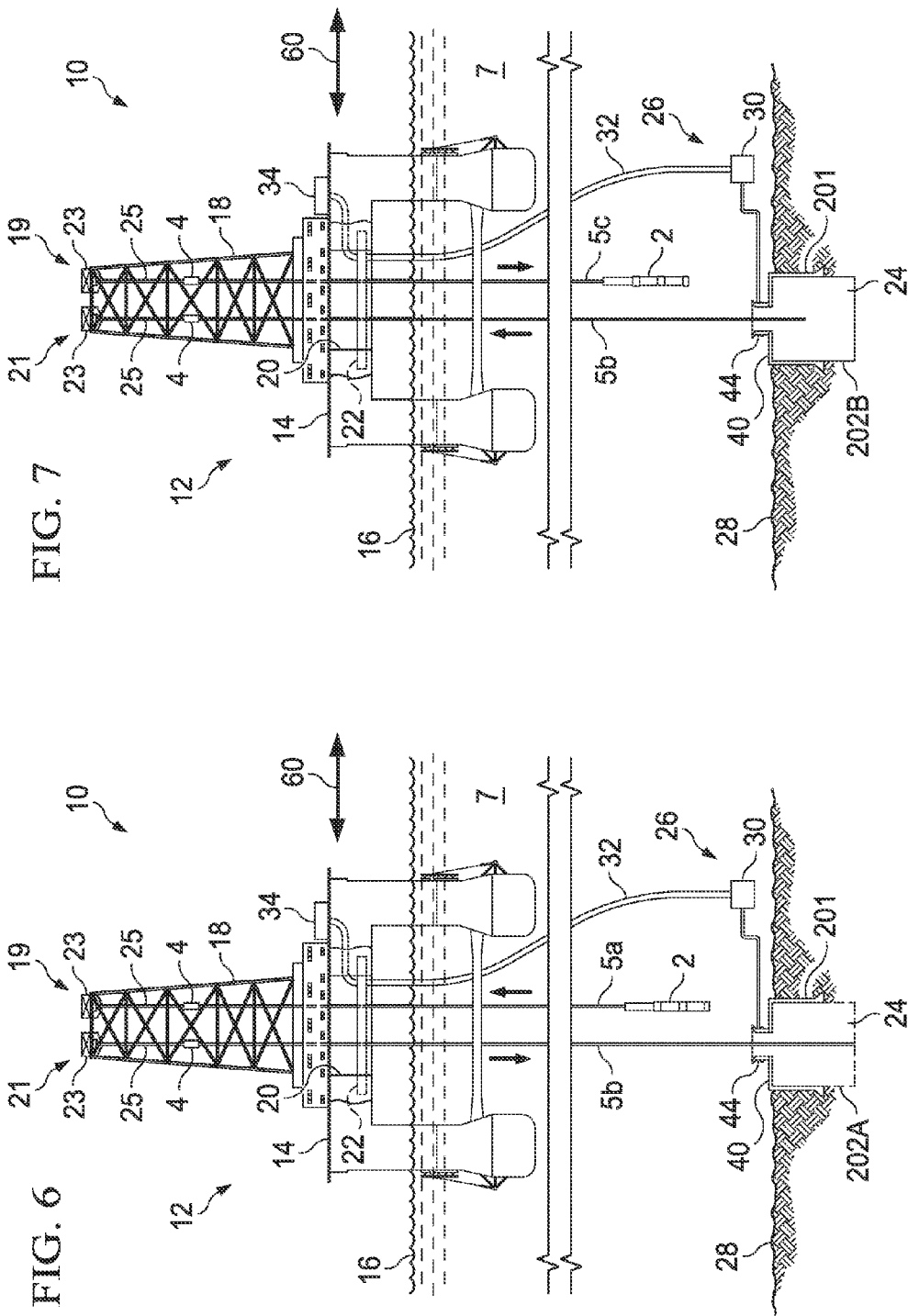
FIG. 7 is a schematic view of a cementing task being performed in the wellbore with the second conveyance assembly, while a subsequent tubular string is being made-up in the water column with the first conveyance assembly, according to one or more aspects of the invention.

In FIG. 7, second conductor 202B is landed and cemented into place. Cementing operations can be performed with conveyance assembly 21 through tubular string 5b in the depicted example. Upon completion of the cementing operation, tubular string 5b is retrieved by second conveyance assembly 21 toward platform 12. While performing wellbore operations via conveyance assembly 21, the subsequent or additional tubular string 5c comprising a device 2 can be made-up via conveyance assembly 19 to drill section 203A, shown in FIG. 8. In FIG. 8, section 203A is being drilled below conductor 202B which is then cemented in place.

FIG. 9 illustrates a tubular string 5d being made-up and run toward wellbore 24 by conveyance assembly 21. In this example, tubular string 5d comprises a length of casing, referred to for purposes of this description as surface casing 203B, that is to be run into and cemented in wellbore section 203A. Section 203A of wellbore 24 is continuing to be drilled by tubular string 5c and conveyance assembly 19 in FIG. 9.

In FIG. 10, the drilling of section 203A is completed and tubular string 5C is pulled out of wellbore 24 at seabed 28. Once tubular string 5c associated with conveyance assembly 19 clears wellbore 24 and enters water column 7 proximate to seabed 28, platform 24 may be positioned (e.g., repositioned) such that the load path (e.g., tubular string 5d) of conveyance assembly 21 is aligned with wellbore 24. The next, or subsequent, tubular string 5d and surface casing 203B can then be lowered into wellbore 24 by conveyance assembly 21. Conveyance assembly 19 continues to retrieve tubular string 5c to platform 12, as conveyance assembly 21 lowers tubular string 5d into wellbore 24 as depicted in FIG. 11.

In FIG. 12, surface casing 203B, which was conveyed by tubular string 5d, is cemented into the wellbore thereby substantially completing the top hole drilling phase of the wellbore in this example of the invention. While cementing surface casing 203B in place, conveyance assembly 19 is making-up tubular string 5e and lowering a mud return module 38 with a valve assembly, such as BOP 36, toward wellbore 24. Once cementing is completed, tubular string 5d will then start retrieving subsea collection device 44. In FIG. 13, tubular string 5d with the subsea mud collection device 44, used in the top hole drilling phase, are continuing to be retrieved to platform 12 by conveyance assembly 21, while a combination of a BOP and a mud return module 38 is being lowered to and landed at wellhead 40 of wellbore 24 by tubular string 5e.

It is emphasized that the invention is not limited to the illustrated examples. As will be understood by those skilled in the art with benefit of this disclosure, the present methods and devices may be implemented in various manners. For example, and without limitation, system 10 can also utilize drilling with casing (e.g., drilling with liner) technology to introduce further efficiencies in the process. The process is generally referred to herein as drilling with casing, however, it will be understood that the process includes drilling with liner, which is utilized in deep water applications. In general, drilling with casing involves drilling and casing a well simultaneously. For example utilizing casing drilling technology, a string of casing, conveyed for example on drillpipe, is utilized to drill a section of the wellbore. Upon completion of the drilled section, all or part of the conveyed casing string can be landed and cemented in the wellbore. By utilizing drilling with casing technology, the number of trips during the drilling process can be reduced. For example, with reference in particular to FIGS. 9 through 12 above, drilling with casing can eliminate the need to run tubular string 5d. Instead, tubular string 5c can deploy the surface string 203B which is then utilized to drill section 203A and which is cemented in place in FIG. 11.

The drilling with casing process can comprise a non-retrievable system or a retrievable bottomhole assembly ("BHA"), for example device 2, illustrated in FIGS. 9-11. In non-retrievable systems, a formation cutting device (e.g., bit, cutter, underreamer) is disposed at the lower end of the casing which is commonly conveyed from a tubular string 5 of drillpipe. In non-retrievable embodiments, the tubular string is rotated and direction control of the trajectory of the drilled wellbore may be limited. When the wellbore is drilled to the casing point, the casing is cemented in place without tripping pipe. Some retrievable systems utilize wire-line conveyed tools which can be retrieved and deployed through the casing via a wire-line. Such retrievable systems can utilize downhole motors to rotate the BHA for drilling and controlling the trajectory of the drilled wellbore. Utilizing retrievable devices or tools facilitates bit changes, thereby providing additional drilling efficiencies without tripping pipe. For example, retrievable tools can facilitate, without limitation, bit and BHA changes, coring, electric logging, and directional drilling. Other retrievable liner drilling systems are premised upon hanging a liner on a drilling assembly conveyed by drillpipe. Such a liner drilling assembly drills the wellbore section in much the same way as a conventional drilling assembly, but it additionally carries the liner with it as it drills. Once the wellbore section is fully drilled, a release mechanism is activated which thereby releases the liner from the drillstring and hangs the liner into the well. Such a release mechanism can be actuated by hydraulic, mechanical, acoustic, or other means. Once the hanger is set in the well, the drillstring and the complete drilling assembly can be retrieved.

A mud return system 26 was described with reference to FIGS. 3-12 for use during the top hole drilling phase of the wellbore. In the top hole drilling phase, mud return system 26 was not fluidicly connected to a safety valve system such as a blowout preventer. However during the bottomhole drilling phase, it is necessary to route the drilling fluid into and out of the wellbore through a safety valve system, such as blowout preventer ("BOP") 36, as shown in FIGS. 14, 15, and 18-34, for example. Therefore in switching from the top hole drilling phase to the bottomhole drilling phase, it is necessary to reconfigure or replace all or part of the top hole drilling phase mud return system 26. An embodiment of the top hole drilling phase mud return system 26, according to one or more aspects of the invention, is illustrated in FIG. 16. One embodiment of a bottomhole drilling phase mud return system 26 is illustrated in FIG. 17.

In FIG. 12, first conveyance assembly 19 is depicted lowering an embodiment of a combination of a BOP and a mud return module 38 (also referred to herein as a "BOP/mud return module") for use during the bottomhole drilling phase. In some embodiments, BOP/mud return module 38 comprises a subsea mud collection device 44 fluidicly connected to BOP 36. In this embodiment, BOP/mud return module 38 is adapted to be fluidicly connected to a mud return conduit 32 and pump 30, subsea. For example, the mud return conduit 32 and pump 30 utilized during the top hole drilling phase that is illustrated disconnected from wellbore 24 in FIG. 12, may be connected to BOP/mud return module 38 subsea, for example by a remotely operated vehicle ("ROV") 9 shown in FIG. 14. In some embodiments, a different pump 30 may be deployed and connected to BOP/mud return module 38, subsea. In other embodiments (not illustrated) a pump 30 and mud return conduit 32 may be assembled as a portion of BOP/mud return module 38 at the surface and then conveyed as part of the modular unit to the wellhead.

Figure 14:
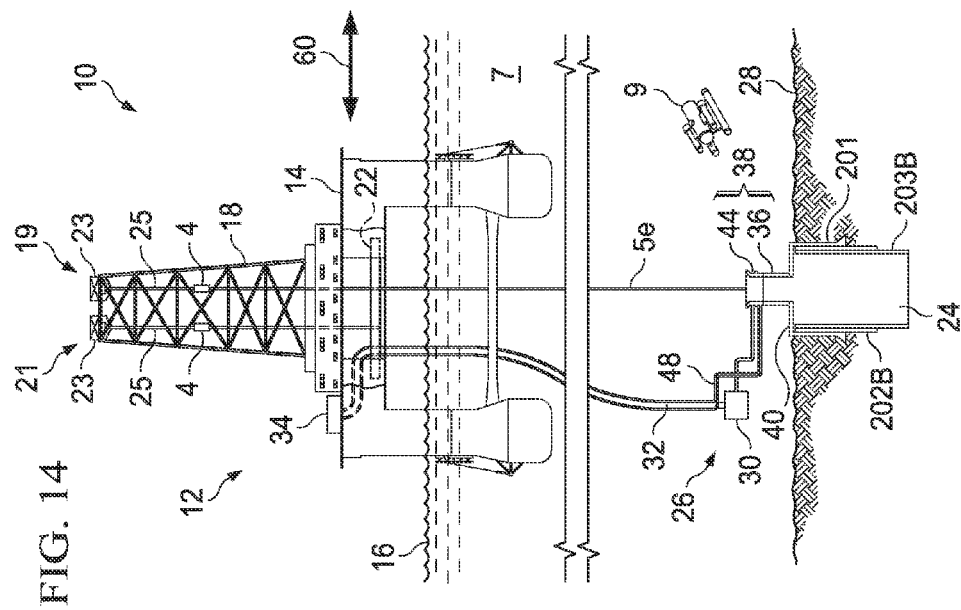
FIG. 14 is a schematic view of the drilling fluid return system for the bottomhole drilling phase connected to the wellbore, according to one or more aspects of the invention.

In FIG. 14, BOP/mud return module 38 is illustrated connected to wellhead 40, and mud return conduit 32 and pump 30 are fluidicly connected with the subsea mud collection device 44 of BOP/mud return module 38. Mud return conduit 32 is connected with surface mud collection device 34 providing mud return system 26.

Figure 15:
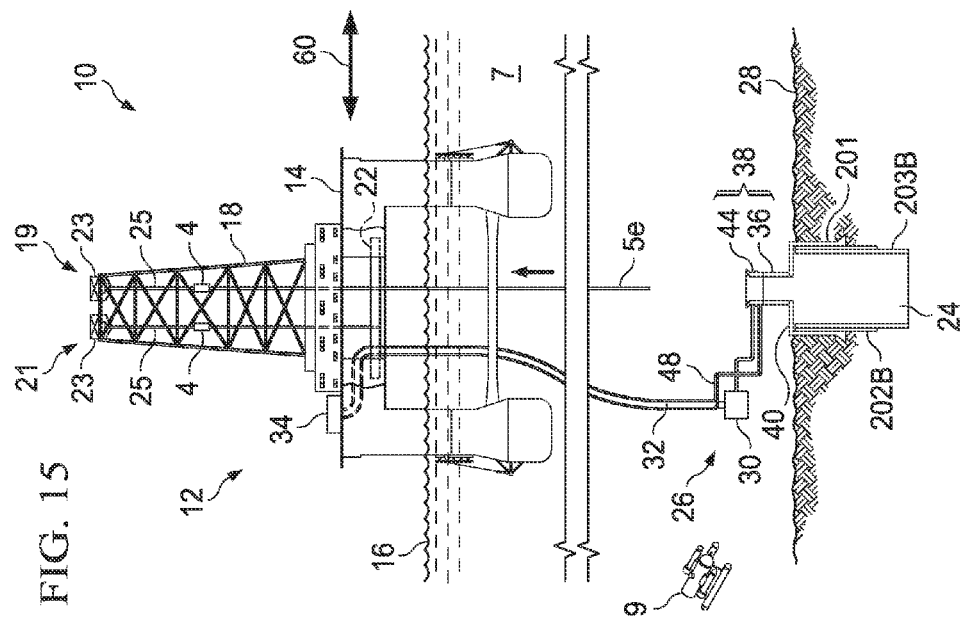
FIG. 15 is a schematic view of the first conveyance assembly retrieving a tubular string, according to one or more aspects of the invention.

FIG. 15 depicts tubular string 5e, which was utilized to deploy BOP/mud return module 38, now disconnected from BOP/mud return module 38, being retrieved by conveyance assembly 19. Mud return conduit 32 and pump 30 are depicted fluidicly connected to wellbore 24 via BOP/mud return module 38. The various subsea devices and systems may be interconnected using ROV 9, for example. Mud return conduit 32, which may have been conveyed for example by conveyance assembly 19, 21, crane, or other mechanism, is illustrated hung (e.g., supported) from structure 22 and moved to a position laterally offset from the load paths between wellbore 24 and conveyance assemblies 19, 21.

Two of the many embodiments of mud return system 26, according to one or more aspects of the invention, are depicted in FIGS. 16 and 17. Some examples of mud return systems that may be utilized in whole or in part according to one or more aspects of the invention are disclosed in U.S. Pat. Nos. 4,149,603, 6,745,851, 7,431,081, and 7,677,329; and U.S. Patent Publication 2009/0032301.

FIG. 16 is a schematic illustration of an embodiment of a portion of a mud return system 26 utilized in the top hole drilling phase, as described for example with reference to FIGS. 3-11. In the depicted embodiment, the top hole drilling phase mud return system 26 comprises a pump 30, mud return conduit 32, and subsea mud collection device 44. Mud return conduit 32 is fluidicly connected to wellbore 24 through subsea mud collection device 44 to return drilling fluid 42 to the surface via pump 30. As previously described, a BOP is not necessary during the top hole drilling phase.

Subsea mud collection device 44 may comprise various apparatus including, without limitation, a fluid sump chamber and/or suction connection for mud return conduit 32. Those skilled in the art will recognize that subsea mud collection device 44 may be connected to the wellbore in various manners. For example, subsea mud collection device 44 may be anchored by a template, or may be physically attached to the wellhead, and/or driven into seabed 28. In FIG. 16, a stabbing guide 46 is attached to subsea mud collection device 44 to aide in stabbing tubular string 5 into wellbore 24 through subsea mud collection device 44. Subsea mud collection device 44 may comprise a sealing portion to segregate drilling fluid 42 from the outside diameter of tubular string 5. In the depicted embodiment, an umbilical 48 (like that depicted in FIG. 17) may run along or near mud return conduit 32 and terminates proximate to subsea mud collection device 44. As shown in FIG. 17, umbilical 48 may comprise one or more power and/or communication lines (e.g., hydraulic, pneumatic, electrical) that may be connected, for example, to pump 30, subsea mud collection device 44 (e.g., control valves, safety valves), as well as to other devices such as, for example, a BOP.

Referring now to FIG. 17, a mud return system 26 according to one or more aspects of the invention is shown being utilized during the bottomhole drilling phase. Subsea mud collection device 44 is fluidicly connected to wellbore 24 via BOP 36. In this embodiment, subsea mud collection device 44 was fluidicly connected and physically secured to BOP 36 at the surface to provide BOP/mud return module 38. BOP/mud return module 38 is attached to wellhead 40, and a stabbing guide 46 is attached to subsea mud collection device 44 to aide in stabbing tubular string 5 into wellbore 24 through BOP 26. Umbilical 48 is depicted having hydraulic control lines extending to BOP 36. As will be understood by those skilled in the art with benefit of this disclosure, subsea mud collection device 44 may comprise a rotating control device ("RCD") through which the tubular strings may be disposed into the wellbore. The RCD can provide sealing to contain the wellbore pressure and permit rotation of the tubular string.

Drilling fluid (e.g., mud) is circulated through the wellbore when the wellbore is being drilled. The drilling fluid serves several purposes including, without limitation, lubricating and cooling the drilling bit, transporting formation cuttings from the wellbore, operating mud motors when used, and controlling the pressure in the wellbore from the surrounding reservoir formations. Typically the drilling fluid is pumped down the tubular string (e.g., drillpipe, casing, liner), utilized for drilling, discharged at the drill bit, and then circulated up the wellbore through the annulus exterior of the drill string to the wellhead. FIG. 16 illustrates an example of drilling fluid 42 being circulated through wellbore 24. In conventional offshore applications, the drilling fluid is often circulated up the annulus of the riser (e.g., between the tubular string and the riser) to the platform. Thus in a typical offshore drilling operation, the drilling fluid is circulated along the load path of the particular conveyance assembly that is performing the wellbore task. According to one or more aspects of the invention, system 10 instead provides a drilling fluid return path (e.g., mud return conduit 32) that is offset from the load path of the conveyance assembly conducting the wellbore operation. The load path of each conveyance assembly 19, 21 is the path in which the suspended tubular string (e.g., operational assembly) travels, and the load paths of each conveyance assembly are different and are laterally offset with respect to each other. For example, in FIG. 18, the load path of conveyance assembly 19 is along tubular string 5f and similarly, the load path of conveyance assembly 21 is along tubular string 5g.

According to one or more aspects of the invention, wellbore system 10 utilizes a dual gradient drilling fluid system. According to one or more aspects of the invention, operation of mud return system 26 can change the pressure of the drilling fluid in the wellbore. For example, with reference to FIG. 18, the distances "H2" and "H1" represent the hydrostatic head in terms of distance from seabed 28 to surface mud collection device 34 (e.g., tanks) which are positioned at platform 12 in the illustrated embodiment. H1 is the hydrostatic head associated with the inlet pressure of the drilling mud to pump 30. H2 is the remaining vertical distance to the surface mud collection device 34. In a conventional riser installation system, the drilling fluid pressure at seabed 28 (e.g., the wellhead) would equal the density of the drilling fluid times the total distance from the wellhead to the surface mud collection device 34. In the present disclosure, the riser is replaced, at least in part, by mud return conduit 32 and pump 30. By controlling the inlet pressure with pump 30, the pressure of drilling fluid 42 at the seabed surface of wellbore 24 can be changed. For example, operating pump 30 substantially eliminates the hydrostatic head H2, and the hydrostatic head H1 is associated with the inlet pressure of pump 30. Further, for example, if drilling fluid 42 is being lost into a formation surrounding wellbore 24, the inlet pressure at pump 30 can be reduced (e.g., by adjusting pump 30), thus lowering the hydrostatic head (H1) to a level effectively below the pressure of the seabed. If additional pressure is needed in the wellbore, for example, to control a pressure kick, the inlet pressure at pump 30 may be increased, effectively moving the hydrostatic head H1 toward the surface. In some embodiments the density of the fluid in return drilling fluid conduit 32 may have a different density, for example a lower density, than the drilling fluids disposed in the tubular string and the wellbore. The demarcation point between the different density fluids can be associated with the demarcation between the hydrostatic head H2 and the hydrostatic head H1.

Figure 18:
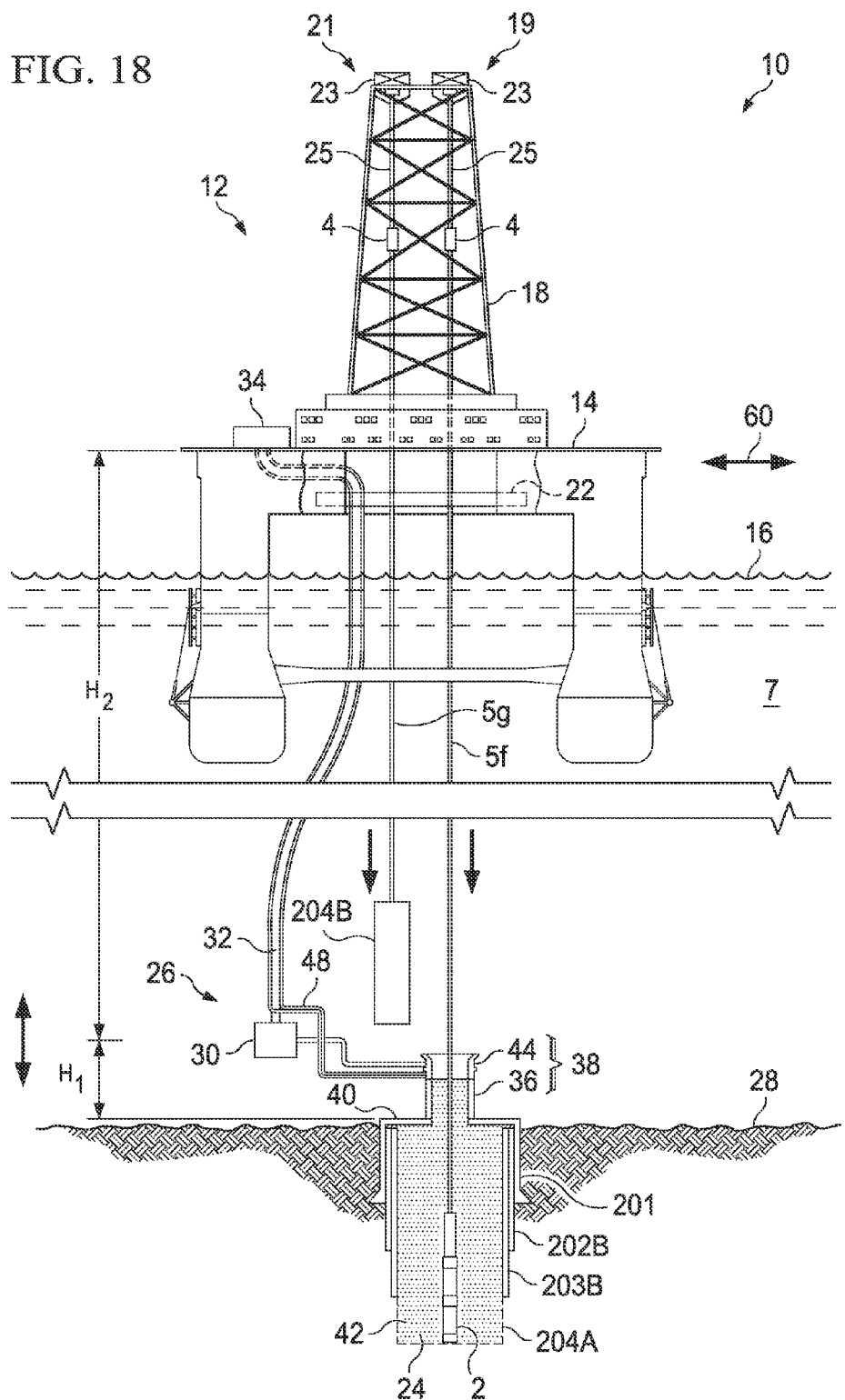
FIG. 18 is a schematic view of a wellbore task during the bottomhole drilling phase that is being performed with the first conveyance assembly, while simultaneously, a tubular string is being made-up in the water column with the second conveyance assembly, according to one or more aspects of the invention.

In FIG. 18, a tubular string 5f (e.g., drilling string) carried by conveyance assembly 19 is stabbed through BOP 36 and into wellbore 24, and then drills wellbore hole section 204A. In other words, entry to the wellbore 24 is performed from the water column (i.e., not from a riser) at an entry point located proximate to seabed 28. In comparison, in a typical prior art drilling system, the tubular string enters the wellbore via a riser, and the entry to the riser and thus the wellbore is located proximate to platform 12 (e.g., the water surface). In contrast, while drilling operations (e.g., a wellbore task) are being performed with conveyance assembly 19, conveyance assembly 21 can be utilized to make-up tubular string 5g in the water column. In this example, tubular string 5g comprises a first liner 204B which is being lowered and which will be run into and cemented in hole section 204A.

Again in comparison to a traditional offshore drilling operation, one or more conveyance assemblies can be making-up tubular strings for use in wellbore 24, while another conveyance assembly is performing operations (e.g., drilling, casing, cementing, etc.) in wellbore 24. More specifically, system 10 facilitates making-up a tubular string in the water column extending substantially all of the distance from the platform to the seabed, while another conveyance assembly is conducting operations in the wellbore. This ability to more fully utilize multiple conveyance assemblies reduces costs and increase efficiency in a number of ways. For example, the process provides the ability to eliminate the time to retrieve and break-out the first tubular string from the seabed, and the time that it takes to make-up an additional string of tubulars to extend from the surface to the seabed. Additionally, making-up tubular string 5g, for example, in the water column eliminates the need and costs of filling and/or circulating a drilling fluid in the tubular string as it is being made-up. The increased efficiency and reduced elapsed time between drilling an open hole section and running and cementing casing also increases efficiency. Additionally, the mud collection system assists in the control of hydrocarbon flows during the drilling and completion of the well.

Figure 19:
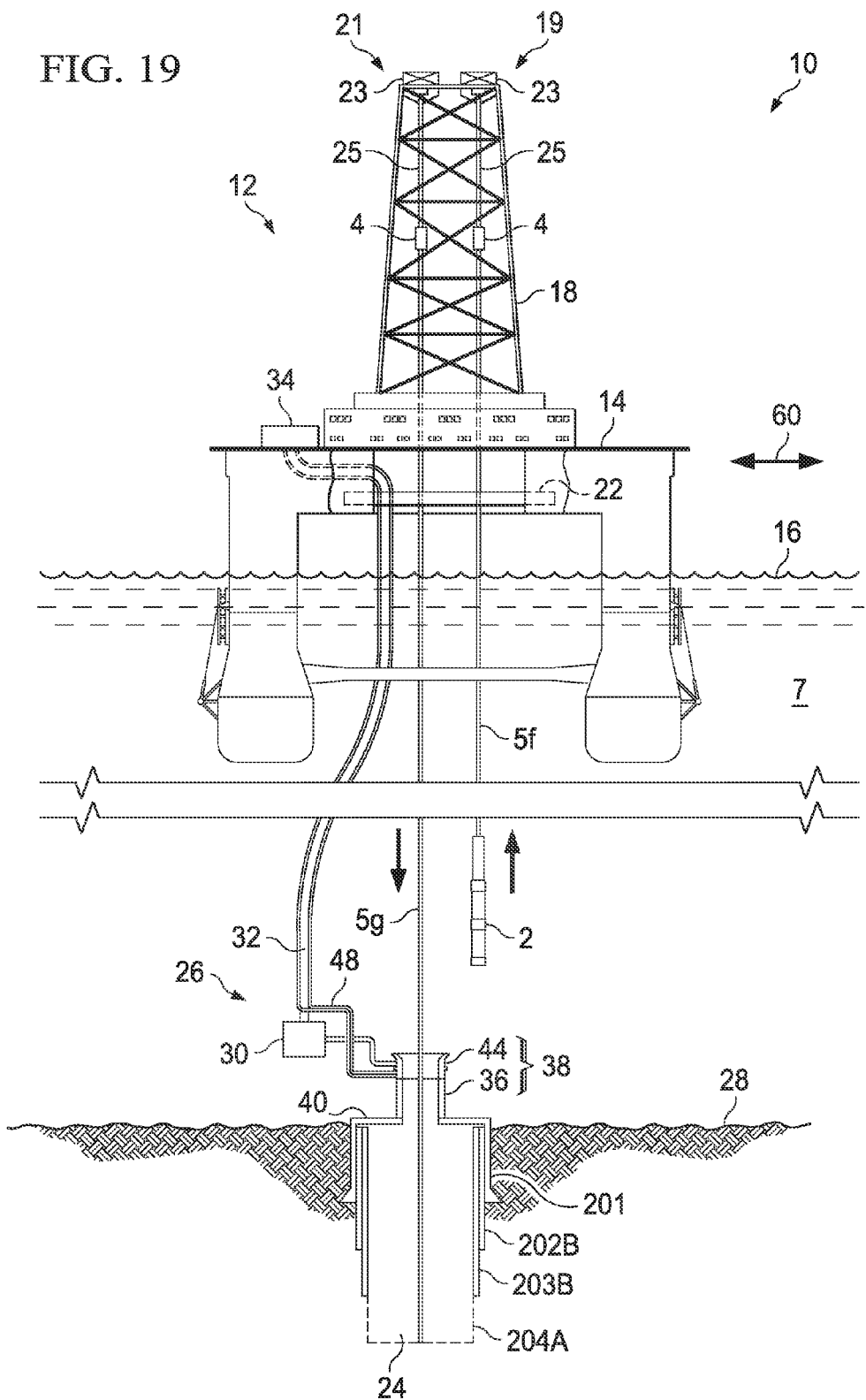
FIG. 19 is a schematic view illustrating a tubular string being withdrawn with the first conveyance assembly from the wellbore proximate to the seabed, while another tubular string is being conveyed from the water column into the blowout preventer and the wellbore, according to one or more aspects of the invention.

Referring now to FIG. 19, the drilling of wellbore section 204A has been completed, and conveyance assembly 19 is withdrawing tubular string 5f from wellbore 24 and BOP 36. Once tubular string 5f is pulled out of BOP 36, subsequent tubular string 5g can then be aligned with the entry point of the BOP, if necessary, and then can be run into BOP 36 and wellbore 24 by conveyance assembly 21. This transition of the prior art entry point into the wellbore from the top of a riser proximate to the water surface 16 to an entry point proximate to seabed 28, as taught and disclosed herein, can save the time normally required to make-up and break-out thousands of feet of tubulars. In FIG. 19, liner 204B (FIGS. 18 and 20) deployed on tubular string 5g is being cemented in wellbore section 204A, while tubular string 5f is being retrieved to the surface by conveyance assembly 19.

FIG. 20 depicts conveyance assembly 21 retrieving tubular string 5g from wellbore 24 after liner 204B has been cemented in wellbore 24. Conveyance assembly 19 is making-up a tubular string 5h in water column 7, while tubular string 5g is being retrieved from wellbore 24 by conveyance assembly 21.

Figure 22:
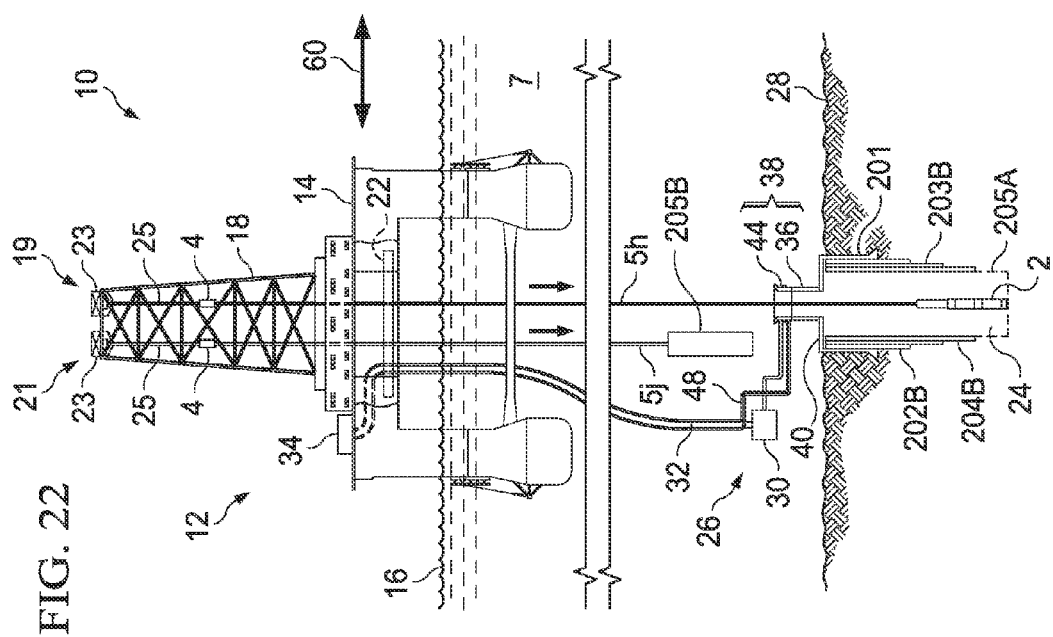
FIG. 22 is a schematic view of additional operations being performed substantially simultaneously and depicts the second conveyance assembly making-up a tubular string, while the string associated with the first conveyance assembly continues to perform a wellbore task, according to one or more aspects of the invention.

FIG. 21 depicts tubular string 5g being pulled (e.g., retrieved) from wellbore 24, and hoisted to platform 12 by conveyance assembly 21 where it may then be, for example, broken-out. Simultaneously, conveyance assembly 19 is running tubular string 5h into wellbore 24 and drilling wellbore section 205A. FIG. 22 depicts conveyance assembly 21 making-up tubular string 5j, while string 5h that is associated with conveyance assembly 19 continues to drill wellbore section 205A. In this example, tubular string 5j comprises an intermediate casing string 205B to be landed, for example, between 6,800 feet (2073 m) to about 14,000 feet (4267 m) below the seabed. liner 204B is deployed on tubular string 5g.

Figure 23:
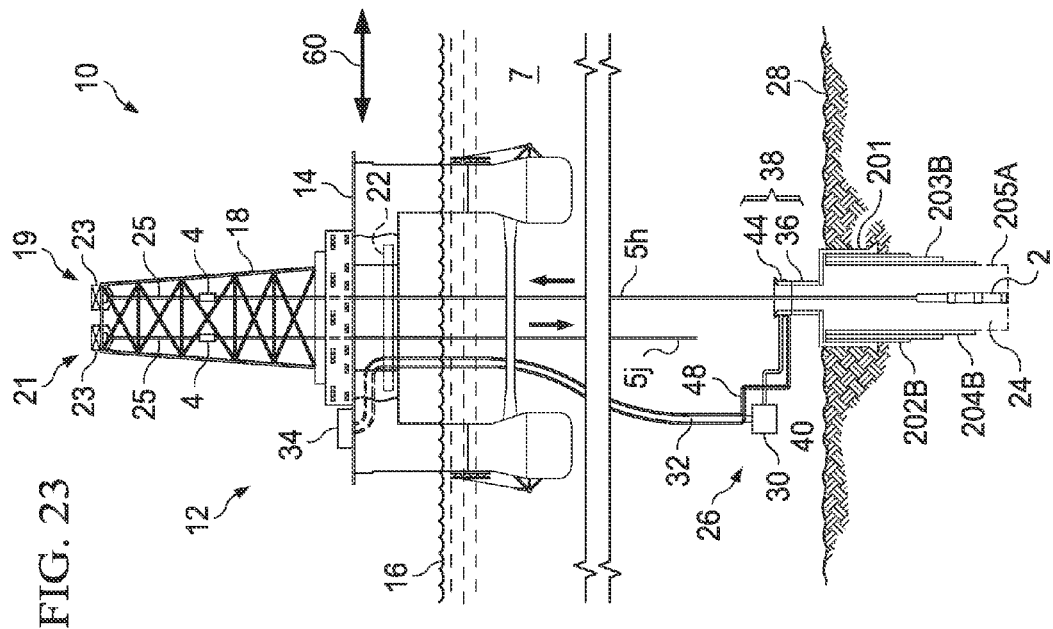
FIG. 23 is a schematic view of additional operations being performed substantially simultaneously and depicts the tubular string associated with one conveyance assembly being withdrawn from the wellbore, while the tubular string associated with other conveyance assembly is being positioned for entry into a BOP, according to one or more aspects of the invention.
Figure 24:
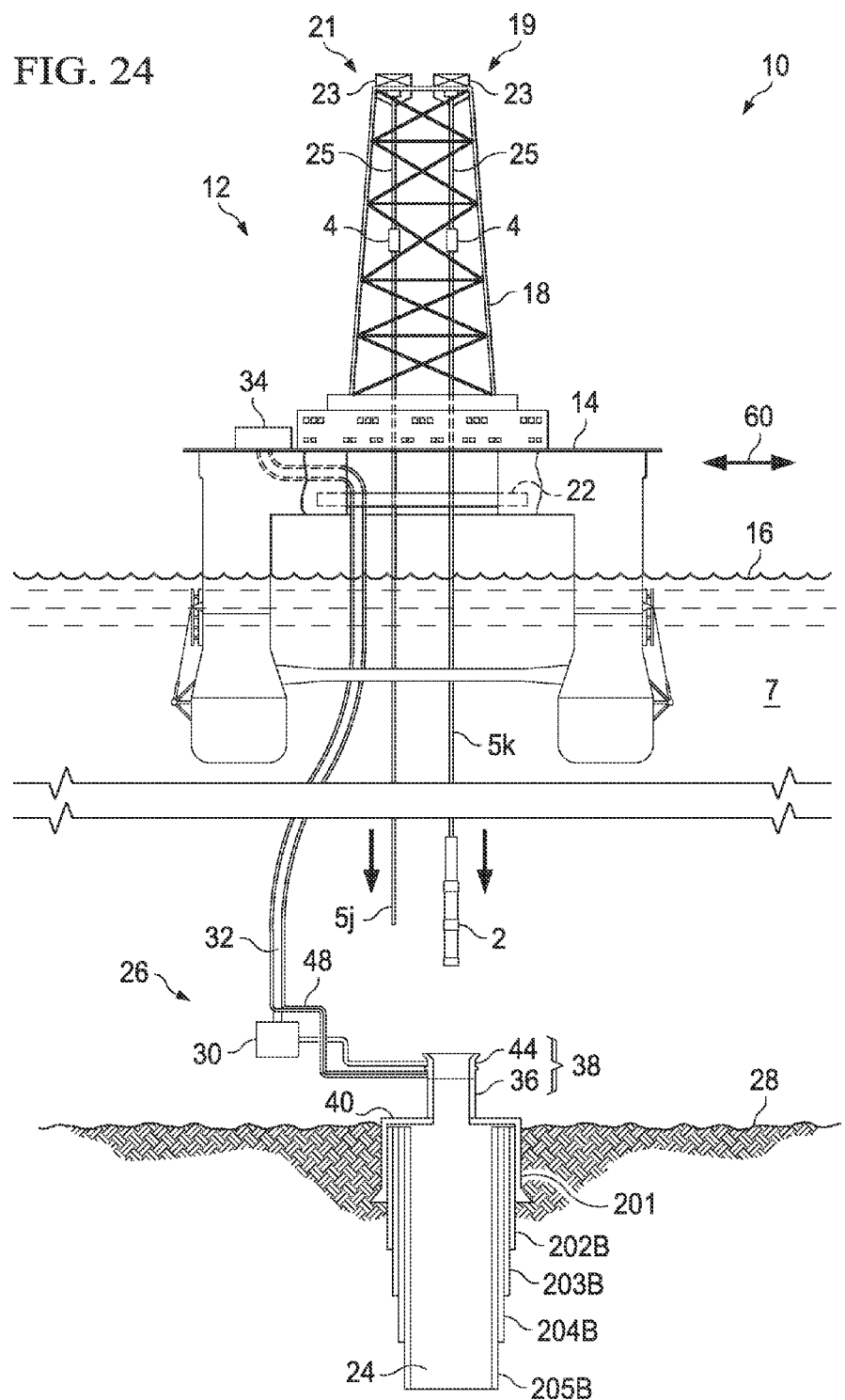
FIG. 24 is a schematic view showing one conveyance assembly completing the cementing of a casing string, while substantially simultaneously the other conveyance assembly is making-up a tubular string, according to one or more aspects of the invention.

After the drilling task is completed, FIG. 23 depicts tubular string 5h being withdrawn from wellbore 24 by conveyance assembly 19, and tubular string 5j is being positioned for stabbing into BOP 36. In FIG. 24, conveyance assembly 21 is deploying intermediate casing string 205B on tubular string 5j and will stab casing string 205B into position in wellbore section 205A; once string 205B is positioned, it will be cemented into place. Simultaneously, conveyance assembly 19 is making-up tubular string 5k.

Figure 25:
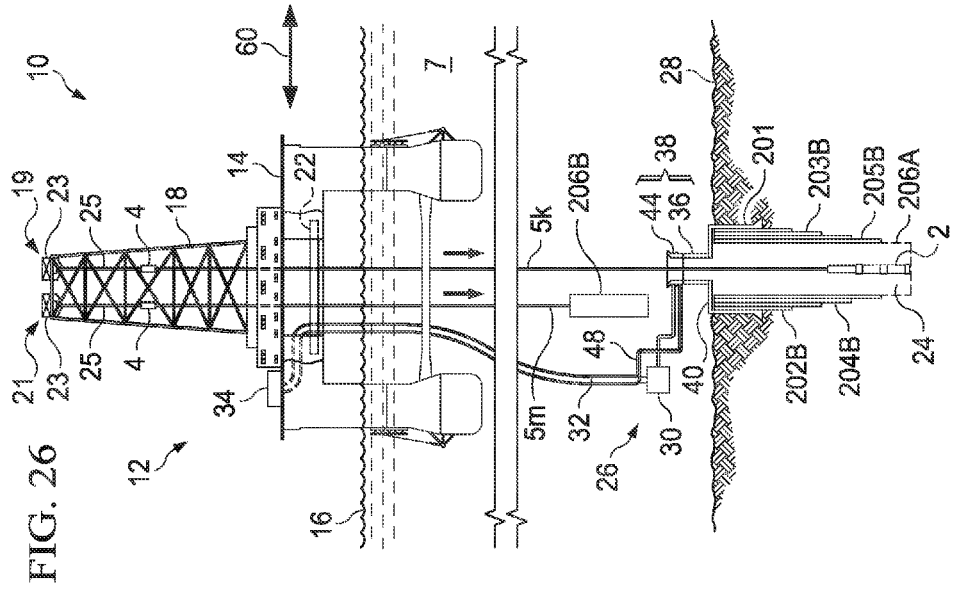
FIG. 25 is a schematic view of additional operations being performed substantially simultaneously by the conveyance assemblies; while one conveyance assembly pulls a tubular string up, the other conveyance assembly stabs a tubular string into the wellbore, according to one or more aspects of the invention.
Figure 26:
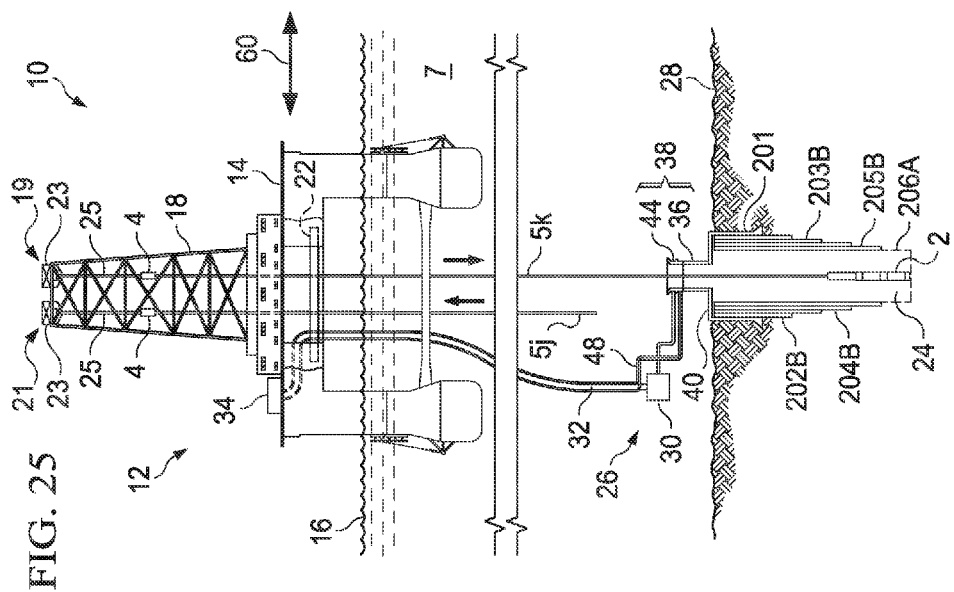
FIG. 26 is a schematic view of additional operations being performed substantially simultaneously by the conveyance assemblies; while one conveyance assembly and string are drilling a wellbore section, the other conveyance assembly is making-up a tubular string, according to one or more aspects of the invention.

As depicted in FIG. 25, upon pulling tubular string 5j from BOP 36 with conveyance assembly 21, conveyance assembly 19 stabs tubular string 5k into BOP 36 and wellbore 24. In FIG. 26, conveyance assembly 19 and tubular string 5k are drilling wellbore section 206A, and conveyance assembly 21 is making-up tubular string 5m comprising a second liner 206B. In FIG. 27, tubular string 5k is removed from wellbore 24 by conveyance assembly 19, and tubular string 5m is run into the wellbore by conveyance assembly 21.

In FIG. 28, string 5m has landed and cemented liner 206B in wellbore section 206A. In the present example, second liner 206B is 11⅞ inch casing extending from about 14,000 feet (4267 m) to about 16,600 feet (4876 m) below seabed 28. Conveyance assembly 21 is depicted retrieving tubular string 5m. Simultaneously, conveyance assembly 19 is making-up tubular string 5n.

Figure 29:
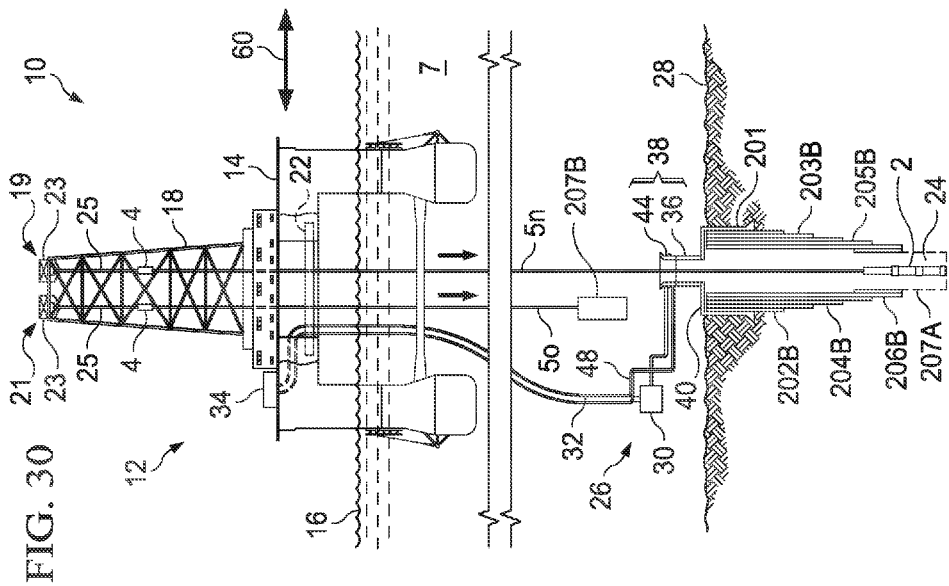
FIG. 29 is a schematic view of additional operations being performed substantially simultaneously by the conveyance assemblies; while one conveyance assembly is retrieving a tubular string, the other conveyance assembly is running another tubular string into the wellbore and performing a wellbore task, according to one or more aspects of the invention.
Figure 30:
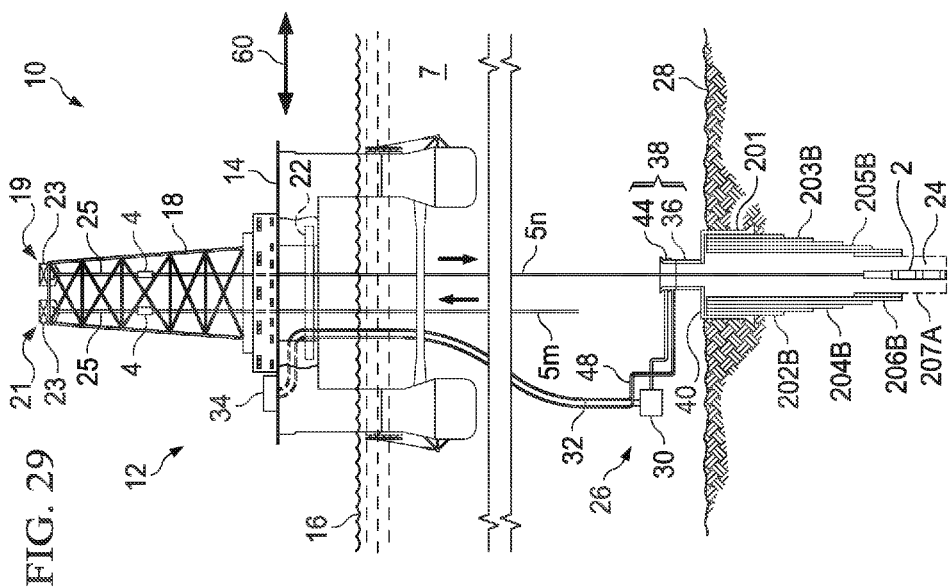
FIG. 30 is a schematic view of additional operations being performed substantially simultaneously by the conveyance assemblies; while one conveyance assembly is associated with a tubular string drilling a wellbore section, the other conveyance assembly is making-up a tubular string, according to one or more aspects of the invention.

FIG. 29, depicts conveyance assembly 21 retrieving tubular string 5m, and conveyance assembly 19 running tubular string 5n into the wellbore and drilling section 207A. In FIG. 30, tubular string 5n is depicted drilling wellbore section 207A, while conveyance assembly 21 is making-up tubular string 5o comprising, for example, production casing 207B.

In FIG. 31, wellbore section 207A has been drilled by tubular string 5n, which is being retrieved to the surface by conveyance assembly 19. Upon clearing BOP 36 with tubular string 5n, platform 12 may be repositioned as needed, and tubular string 5o can be run into the wellbore by conveyance assembly 21.

In FIG. 32, conveyance assembly 19 continues to retrieve tubular string 5n, and tubular string 5o is being run into the wellbore by conveyance assembly 21. In FIG. 33, tubular string 5o has landed and cemented production casing 207B, and is being retrieved by conveyance assembly 21. Simultaneously, conveyance assembly 19 is making-up tubular string 5p to retrieve BOP 36.

In FIG. 34, once the well is completed, tubular string 5p is connected to BOP 36, for example with the assistance of a ROV 9. Pump 30 will then be retrieved with mud return conduit 32, although other means, including tethers, may be utilized. Once the BOP is removed from the well, a valve manifold (such as a Christmas tree) needs to be installed on the wellbore. As described with reference to the previous Figures, the Christmas tree can be rigged up and run down to the wellbore by conveyance assembly 21, while conveyance assembly 19 retrieves BOP 36 (e.g., BOP/mud return module 38).

Figure 35:
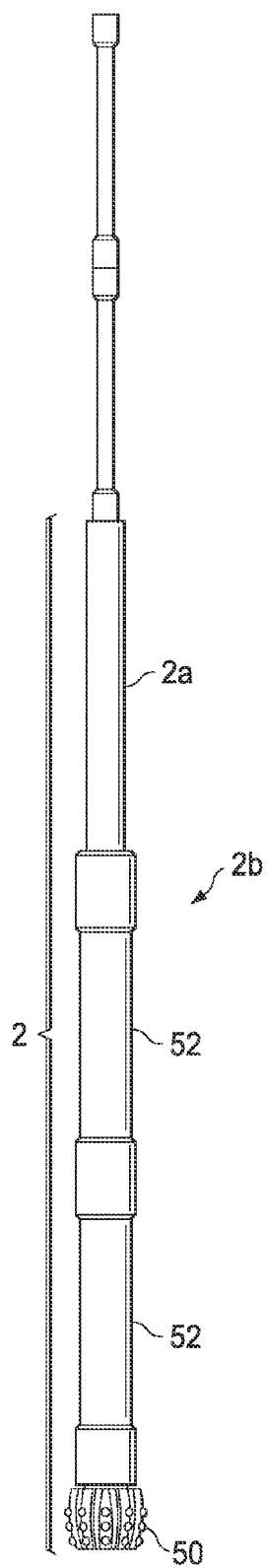
FIG. 35 is a schematic view of an embodiment of a tubular string and bottomhole assembly, according to one or more aspects of the invention.

FIG. 35 is a schematic illustration of a tubular string 5, according to one or more aspects of the invention. In the depicted embodiment, tubular string 5 comprises an operational device 2 connected to the terminal end of a string of drillpipe. In this example, device 2 comprises heavy weight drillpipe 2a and a bottomhole assembly ("BHA") 2b. BHA 2b comprises a cutting device 50 (e.g., drillbit, underreamer), and can comprise one or more operational devices 52. Operational devices 52 include, without limitation, logging instruments (e.g., logging-while-drilling; measurement-while-drilling), motors (e.g., mud motor), fluid sampling tools, electronic packages, valves, actuators, and various telemetry instruments (e.g., mud pulse devices).

Figure 36:
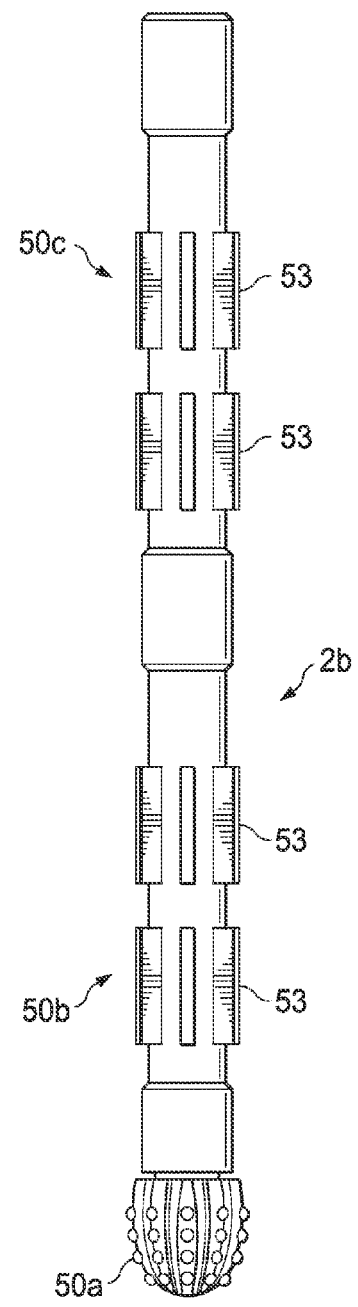
FIG. 36 is a schematic view of an embodiment of a bottomhole assembly, according to one or more aspects of the invention.

FIG. 36 is a schematic illustration of an embodiment of a BHA 2b, according to one or more aspects of the invention. The depicted BHA 2b of FIG. 36, is adapted to be modified subsea without tripping pipe or retrieving BHA 2b. For example, the depicted BHA 2b is adapted to be modified by a remotely operated vehicle ("ROV"), or the like. For example, BHA 2b comprises pilot cutter 50a, and one or more additional cutting devices depicted as 50b and 50c, all of which have different cutting diameters. For example, in the depicted embodiment, cutter 50c has a cutting diameter greater than the cutting diameter of cutter 50b, which has a greater cutting diameter than pilot cutter 50a. In one embodiment, additional cutters 50b, 50c each comprise blades 53. In one embodiment, blades 53 are removably attached to the body 54 of BHA 2b. For example after a wellbore section has been drilled utilizing cutters 53c, BHA 2 can be retrieved from the wellbore, and an ROV can be utilized to remove larger diameter cutter 50c. BHA 2b can then be run back into the wellbore, and a wellbore section can be drilled with cutter 50b. BHA 2b can then be retrieved from the wellbore, and within the water column, blades 53 of cutter 50b can be removed. In this embodiment, BHA 2b can then be utilized to drill an additional wellbore section utilizing pilot cutter 50a.

In another embodiment, blades 53 can be radially retracted and/or extended relative to body 54. For example, utilizing an ROV and/or an operational device disposed with BHA 2b, the different diameter cutters can be utilized in the manner described above with reference to the removable blades 53. Operational devices for actuating blades 53 radially relative to body 54 can include, without limitation, electric, fluidic, and mechanical actuators.

The foregoing outlines features of several embodiments so that those skilled in the art may better understand the aspects of the invention. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the invention, and that they may make various changes, substitutions and alterations herein without departing from the spirit and scope of the invention. The scope of the invention should be determined only by the language of the claims that follow. The term "comprising" within the claims is intended to mean "including at least" such that the recited listing of elements in a claim are an open group. The terms "a," "an" and other singular terms are intended to include the plural forms thereof unless specifically excluded.

What is claimed is:

1. A method for drilling an offshore wellbore at a single wellhead into a seabed from a platform positioned proximate to a water surface and above a water column, comprising:
   withdrawing, with a first conveyance assembly, a first tubular string from the wellbore into the water column at a location proximate to the seabed;
   running, with a second conveyance assembly, a second tubular string into the water column and then the wellbore at the location proximate to the seabed after withdrawing the first tubular string from the wellbore with the first conveyance assembly; and
   wherein each conveyance assembly has a load path and wherein a load path of the first conveyance assembly is laterally offset from a load path of the second conveyance assembly, and wherein the alternating of operations conducted in the wellbore from the first conveyance assembly and the second conveyance assembly can continue through both the top hole drilling phase and the bottom hole drilling phase through a blowout preventer until the well is completed.

2. The method of claim 1, further comprising:
performing a task in the wellbore with the first tubular string disposed in the wellbore; and
making-up at least a portion of the second tubular string in a water column between the water surface and the seabed with the second conveyance assembly, while performing the task in the wellbore with the first tubular string.

3. The method of claim 2, wherein the task comprises one selected from the group of drilling, casing, and cementing.

4. The method of claim 1, further comprising establishing a drilling fluid return path from the wellbore, whereby the drilling fluid return path is laterally offset from a load path of the first and the second conveyance assemblies.

5. The method of claim 4, wherein establishing the offset drilling fluid return path comprises establishing fluid connection to the wellbore via a valve.

6. The method of claim 4, further comprising:
performing a task in the wellbore with the first tubular string disposed in the wellbore prior to withdrawing the first tubular string with the first conveyance assembly; and
making-up at least part of the second tubular string in the water column between the water surface and the seabed, while performing the task in the wellbore with the first tubular string.

7. The method of claim 4, wherein the task comprises one selected from the group of drilling, casing, and cementing.

8. The method of claim 6, wherein establishing the offset drilling fluid return path comprises establishing fluid connection to the wellbore via a valve.

9. The method of claim 3, further comprising:
performing a task in the wellbore with the second tubular string disposed in the wellbore, and after completion of the task, withdrawing with the second conveyance assembly, the second tubular string from the wellbore at a location proximate to the seabed;
running, with the first conveyance assembly, a subsequent tubular string into the wellbore at the location proximate to the seabed after the second tubular string is withdrawn from the wellbore; and
continuing to run tubular strings into the wellbore in a substantially alternating sequence with the first conveyance assembly and the second conveyance assembly, until the well is completed.

10. The method of claim 1, wherein the first conveyance assembly and the second conveyance assembly are disposed in a multi-activity derrick.

11. A method for drilling an offshore wellbore at a single wellhead into a seabed from a platform positioned proximate to a water surface and above a water column, comprising:
positioning a platform comprising a first conveyance assembly and a second conveyance assembly above a desired location of a wellbore;
running a first tubular string from a first conveyance assembly into the water column and to the seabed;
forming a first wellbore section utilizing the first conveyance assembly and the first tubular string;
making-up a second tubular string with the second conveyance assembly in the water column to a position proximate to the seabed, wherein a portion of making-up the second tubular string is performed while the first conveyance assembly is forming the first wellbore section;
withdrawing the first tubular string from the wellbore into the water column at a location proximate to the seabed, with the first conveyance assembly; and
running the second tubular string into the wellbore at the location proximate to the seabed with the second conveyance assembly, after the first tubular string is withdrawn from the wellbore with the first conveyance assembly, wherein the alternating of operations conducted in the wellbore from the first conveyance assembly and the second conveyance assembly can continue through both the top hole drilling phase and the bottom hole drilling phase through a blowout preventer until the well is completed.

12. The method of claim 11, further comprising establishing a drilling fluid return path, whereby the drilling fluid path is laterally offset from a load path of the first and the second conveyance assemblies to the wellbore.

13. The method of claim 12, wherein establishing the offset drilling fluid return path comprises: installing a conduit fluidically connected to the wellbore; and fluidicly connecting the conduit to a pump.

14. The method of claim 13, wherein the pump is positioned below the water surface.

15. The method of claim 11, wherein the first wellbore section is formed prior to installing a valve on the wellbore.

16. The method of claim 11, further comprising installing a valve on the wellbore, wherein the forming of the first wellbore section is performed after installing the valve on the wellbore.

17. The method of claim 16, further comprising:
withdrawing, with the second conveyance assembly, the second tubular string from the wellbore at a location proximate to the seabed;
running, with the first conveyance assembly, a subsequent tubular string into the wellbore at the location proximate to the seabed after the second tubular string has been withdrawn from the wellbore; and
continuing to run tubular strings into the wellbore in a substantially alternating sequence with the first conveyance assembly and the second conveyance assembly until the well is completed.

18. A method for drilling an offshore wellbore at a single wellhead into a seabed from a platform positioned proximate to the water surface and above a water column, comprising:
making-up a first tubular string with a first conveyance assembly;
running the first tubular string into the water column and then into the wellbore, wherein the first tubular string enters the wellbore from the water column at an entry point proximate to the seabed;
performing a wellbore task with the first tubular string;
making-up at least a portion of a second tubular string in the water column with a second conveyance assembly while the task is being performed in the wellbore with the first tubular string;
once the wellbore task has been performed with the first tubular string, withdrawing the first tubular string from the wellbore and into the water column with the first conveyance assembly; and
running the second tubular string into the wellbore at the entry point from the water column with the second conveyance assembly, wherein the alternating of operations conducted in the wellbore from the first conveyance assembly and the second conveyance assembly can continue through both the top hole drilling phase and the bottom hole drilling phase through a blowout preventer until the well is completed.

19. The method of claim 18, wherein at least a portion of the making-up of the second tubular string in the water column is performed simultaneously with the performing of the wellbore task with the first tubular string.

20. The method of claim 18, wherein the entry point into the wellbore is a blowout preventer.

21. The method of claim 20, further comprising returning a drilling fluid from the wellbore via a drilling fluid return conduit that is offset from the load path of the first and the second conveyance assemblies and the wellbore.

22. The method of claim 21, further comprising:
fluidicly connecting the fluid return conduit to the wellbore through a pump and the blowout preventer, wherein the pump is disposed proximate to the seabed; and
controlling an inlet pressure of the returning drilling fluid to the pump in response to a wellbore condition.

23. The method of claim 22, further comprising adjusting the pump to lower the inlet pressure of the returning drilling fluid in response to losing drilling fluid in the wellbore.

24. The method of claim 18, further comprising:
withdrawing, with the second conveyance assembly, the second tubular string from the wellbore at a location proximate to the seabed;
running, with the first conveyance assembly, a subsequent tubular string into the wellbore at the entry point proximate to the seabed after withdrawing the second tubular string from the wellbore; and
continuing to run tubular strings into the wellbore in a substantially alternating sequence with the first conveyance assembly and the second conveyance assembly until the well is completed.

* * * * *